(12) United States Patent
Grundeman et al.

(10) Patent No.: US 10,583,003 B2
(45) Date of Patent: Mar. 10, 2020

(54) METHOD OF MAKING A PROSTHETIC VALVE AND VALVE OBTAINED THEREWITH

(71) Applicant: DSM IP Assets B.V., Heerlen (NL)

(72) Inventors: Paul Frederik Grundeman, Utrecht (NL); Jolanda Kluin, Utrecht (NL); Karlien Kristel Boon-Ceelen, Echt (NL); Thomas König, Utrecht (NL)

(73) Assignee: DSM IP ASSETS B.V., Heerlen (NL)

( * ) Notice: Subject to any disclaimer, the term of this patent is extended or adjusted under 35 U.S.C. 154(b) by 24 days.

(21) Appl. No.: 15/309,030

(22) PCT Filed: May 6, 2015

(86) PCT No.: PCT/EP2015/059986
§ 371 (c)(1),
(2) Date: Nov. 4, 2016

(87) PCT Pub. No.: WO2015/169870
PCT Pub. Date: Nov. 12, 2015

(65) Prior Publication Data
US 2017/0065408 A1   Mar. 9, 2017

(30) Foreign Application Priority Data

May 6, 2014   (EP) .................................. 14167269
May 6, 2014   (EP) .................................. 14167270
(Continued)

(51) Int. Cl.
*A61F 2/24*   (2006.01)

(52) U.S. Cl.
CPC .......... *A61F 2/2415* (2013.01); *A61F 2/2412* (2013.01); *A61F 2/2418* (2013.01); *A61F 2220/0075* (2013.01)

(58) Field of Classification Search
CPC .................. A61F 2/2418; A61F 2/2412; A61F 2220/0075; A61F 2/2409; A61F 2/24; A61F 2250/006
See application file for complete search history.

(56) References Cited

U.S. PATENT DOCUMENTS

| 3,526,906 A | 9/1970 | DeLaszlo |
| 3,859,668 A | 1/1975 | Anderson |

(Continued)

FOREIGN PATENT DOCUMENTS

| NL | 1008349 | 8/1999 |
| WO | 2000/062714 | 10/2000 |

(Continued)

OTHER PUBLICATIONS

International Search Report and Written Opinion of the ISA for PCT/EP2015/059986, dated Jul. 20. 2015, 9 pages.
(Continued)

*Primary Examiner* — Ann Schillinger
(74) *Attorney, Agent, or Firm* — Nixon & Vanderhye P.C.

(57) ABSTRACT

The present relates to a method of making a prosthetic valve that can take a first form wherein the valve is open and a second form wherein the valve is closed, the valve comprising a leaflet, a supporting element, and a stent to which the leaflet and supporting element are attached, the leaflet having a free margin that can move between a first position wherein the valve takes the first form and a second position wherein the valve takes the second form, the method comprising:—providing a woven textile structure,—forming the leaflet and the supporting element from this textile structure, such that a selvedge of the textile structure forms the free margin of the leaflet, and—forming the valve therewith, wherein the textile structure has a single layer thickness of between 40 to 150 μm and comprises yarn comprising polymeric filaments, the yarn having a linear density of less (Continued)

than 120 dtex and an elongation at break of 10% or less, and wherein the leaflet is attached to the stent by making stitches through at least 2 layers of the woven textile structure to form a commissure. The woven fabric used method is thin and flexible, and allows stitching through multiple layers to result in durable performance of both leaflets and commissures in actual use. The invention also relates to a prosthetic valve as obtainable by said method.

14 Claims, 17 Drawing Sheets

(30) Foreign Application Priority Data

May 6, 2014 (EP) .................................... 14167271
May 6, 2014 (EP) .................................... 14167272

(56) References Cited

U.S. PATENT DOCUMENTS

| | | | |
|---|---|---|---|
| 4,035,849 A | | 7/1977 | Angell et al. |
| 4,191,218 A | | 3/1980 | Clark et al. |
| 4,610,688 A | | 9/1986 | Silvestrini et al. |
| 5,500,014 A | | 3/1996 | Quijano et al. |
| 5,800,514 A | | 9/1998 | Nuñez et al. |
| 5,855,602 A | * | 1/1999 | Angell .................. A61F 2/2409 |
| | | | 606/1 |
| 6,283,995 B1 | | 9/2001 | Moe et al. |
| 6,454,799 B1 | | 9/2002 | Schreck |
| 6,726,715 B2 | | 4/2004 | Sutherland |
| 10,039,640 B2 | | 8/2018 | Grundeman et al. |
| 2003/0114924 A1 | | 6/2003 | Moe |
| 2004/0176658 A1 | | 9/2004 | McMurray |
| 2005/0027348 A1 | | 2/2005 | Case et al. |
| 2005/0137681 A1 | | 6/2005 | Shoemaker et al. |
| 2005/0177227 A1 | * | 8/2005 | Heim .................. A61F 2/2412 |
| | | | 623/2.12 |
| 2005/0228487 A1 | | 10/2005 | Kujawski |
| 2006/0085080 A1 | * | 4/2006 | Bechgaard .......... A61F 2/30721 |
| | | | 623/23.43 |
| 2008/0200977 A1 | | 8/2008 | Paul et al. |
| 2008/0275540 A1 | | 11/2008 | Wen |
| 2009/0012251 A1 | * | 1/2009 | Dirks ........................ D01F 6/04 |
| | | | 526/352 |
| 2009/0276039 A1 | | 11/2009 | Meretei |
| 2011/0282440 A1 | | 11/2011 | Cao et al. |
| 2012/0172978 A1 | | 7/2012 | Dumontelle |
| 2013/0073037 A1 | | 3/2013 | Gregg et al. |
| 2014/0135906 A1 | | 5/2014 | Winner et al. |
| 2016/0038280 A1 | * | 2/2016 | Morriss .................. A61F 2/2436 |
| | | | 623/2.18 |
| 2017/0065408 A1 | | 3/2017 | Grundeman et al. |
| 2017/0189172 A1 | | 7/2017 | Grundeman et al. |

FOREIGN PATENT DOCUMENTS

| | | |
|---|---|---|
| WO | 2004/032987 | 4/2004 |
| WO | 2010/020660 | 2/2010 |
| WO | WO 2010/020660 | 2/2010 |
| WO | 2012/177942 | 12/2012 |
| WO | 2013/013032 | 1/2013 |

OTHER PUBLICATIONS

Heim et al, "Textile Heart Valve: Novel Shaping Process and Material Performances", Materials and Manufacturing Processes, 26:1303-1309 2011.

Zaidi et al, "Preliminary experience with porcine intestinal submucosa (CorMatrix) for valve reconstruction in congenital heart disease: Histologic evaluation of explanted valves", The Journal of Thoracic and Cardiovascular Surgery, vol. 148, No. 5, pp. 2217-2225 (Nov. 2014).

http://www.cs.arizona.edu/patterns/weaving/webdocs/opr_rgdw.pdf (Oct. 5, 2002).

JP Application No. 2016-564324, Notice of Reasons for Rejection, dated Mar. 26, 2019.

JP Application No. 2016-564298, Notice of Reasons for Rejection, dated Apr. 2, 2019.

* cited by examiner

METHOD OF MAKING A PROSTHETIC VALVE AND VALVE OBTAINED THEREWITH

This application is the U.S. national phase of International Application No. PCT/EP2015/059986 filed 6 May 2015, which designated the U.S. and claims priority to EP Patent Application Nos. 14167271.7 filed 6 May 2014, 14167270.9 filed 6 May 2014, 14167269.1 filed 6 May 2014, and 14167272.5 filed 6 May 2014, the entire contents of each of which are hereby incorporated by reference.

GENERAL FIELD OF THE INVENTION

The invention relates to implantable medical devices and methods of making such medical devices, like a prosthetic valve and more specifically a two- or three-leaflet prosthetic heart valve.

BACKGROUND

A typical natural valve of a mammal is the aortic valve, one of the four heart valves. The aortic valve comprises three leaflets, also called cusps, attached to the aortic root that serves as a supporting element for these leaflets. Each of the three leaflets of the aortic valve has a free margin and a margin where it is attached in semilunar fashion to the aortic root. When the valve opens, the leaflets fall back into their sinuses without the potential of occluding any coronary orifice. The hingelines of adjacent leaflets meet at the level of the sinutubular junction, forming at least part of the commissures. The body of a leaflet is pliable, extendable and thin to provide the required flexibility, although its thickness is not uniform. The leaflet is slightly thicker towards its free margin. On its ventricular surface is the zone of apposition, known as the lunule, occupying the full width along the free margin and spanning approximately one-third of the depth of the leaflet. This is where the leaflet meets the adjacent leaflets during valvular closure. With the valve in closed position, the margins of the lunules meet together, separating blood in the left ventricular cavity of the heart from blood in the aorta. For a valve of this type, or a corresponding type, highest mechanical stresses during opening and closing occur at the commissures and, to a lesser extent, at the free margin of the leaflets.

Prosthetic valves are implanted in the human or animal body and may for instance be used as a passive, one direction prosthetic valve within or nearby blood vessels. They can be completely preformed and implanted as such, or formed in situ using the artificial and/or natural parts needed to form a functional prosthetic valve. A suitable prosthetic valve needs to open and close readily in response to differential pressure on either side of the valve, cause no or only little non-physiological turbulence in the blood flow, and avoid too much regurgitation. Cardiovascular products, such as heart valve prostheses, are thus subject to high requirements with respect to loading conditions, both in magnitude as in number of cycles. Typically, heart valve leaflets may undergo over a billion load cycles in their lifetime. Durability of prosthetic valves, especially of moving leaflets, is therefore an important requirement.

Any prosthetic valve should be able to resist the actual mechanical load on the commissures and leaflet free margin during valvular operation and preferably, maintain to resist such cyclical load during many years. For this, not only initial strength is an important parameter but also reducing the chances of (non-apparent) production anomalies in making the valve.

Today, valves used in valve surgery typically are bioprosthetic valves having leaflets made from biological tissue, often chemically treated bovine pericardium. This is an elastic material that performs relatively well and is able to mimic the natural valve. However, early failure is often encountered, and is believed to be associated with high stresses on the leaflet material upon continuous stretching and retracting under pulsatile load. Various synthetic materials and designs have been proposed as alternatives for making leaflets of prosthetic valves.

A valve prosthesis made using synthetic fibers is for example described in NL1008349. This valve comprises a supporting element carrying a number of leaflets, which have been made by winding reinforcing fibers onto a mandrel in specific directions corresponding to the occurring stresses in the leaflets. Since the fibers have to be positioned according to the maximum stress lines, this valve prosthesis is difficult to make and uses many wound layers to accommodate stresses, whereby mass is added.

Similarly, U.S. Pat. No. 6,726,715 describes a leaflet for a heart valve comprising a flexible sheet having stress-relieving fibrous elements aligned with predetermined stress lines in the leaflet during valve operation. Sheet material is typically PTFE or PVF, with high-strength/high-modulus fibers as reinforcing elements. Fibers such as carbon, aramid, or polyethylene fibers like Dyneema® UHMWPE fibers may be used.

WO2010/020660 describes a prosthetic valve made from a uniform hollow braid made from polyolefin fibers. The hollow braid is shaped to form a valve by pulling the hollow braid over a mould, comprising a tubular part and a star-shaped part. By subsequently applying heat and pressure, the hollow braid takes the shape of the mould and different sections are created. Around the tubular part of the mould the braid forms into a section that corresponds to a supporting element of the valve, whereas a star shaped part of the mould provides a section that corresponds to multiple valve leaflets. Before removing the valve from the mould, the front and back sides of the valve prosthesis are edge trimmed. To prevent disruption of the trimmed edge, the edge may be heat treated to melt fuse the yarns to each other, provided with a stitching, or otherwise treated to make the edge mechanically stable.

Heim et al. in *Materials and Manufacturing Processes*, 26: 1303-1309, 2011 disclose a method wherein artificial leaflets are made from woven polyester yarns by thermally shaping the woven textile on a mould into a three-cusp geometry; showing that woven polyester could be suited to form a valve prosthesis. Polyester yarn has stretching properties such that the woven textile is able to mimic the natural elastic stretching of a human valve (about 15% of elongation), due to its typical elongation at break of about 14-17%. In order to obtain a valve with good contact between leaflets in closed position and to limit stresses during working cycles, the authors teach to shape the leaflets such that there is a fairly large inherent opening in the centre of the valve, whereas under cardiac pulsatile load adequate coaptation is created over the length of the free margin of the leaflets to prevent or at least minimize regurgitation.

In US2005/0137681 a venous valve with a tubular frame and a cover is disclosed, which cover includes surfaces defining a reversibly sealable opening and thus acting as leaflets. The leaflets can have various sizes and shapes, including arcuate edges, curved surfaces, a concave structure, or include a curved support structure to efficiently close the valve and restrict retrograde fluid flow. Leaflets may be made of biologic or synthetic fluid-impermeable material, including ePTFE, PET, urethane and polyethylene.

WO2000/62714 discloses a heart valve prosthesis including a one-piece moulded body with a plurality of leaflets, made from a silicone or polyurethane. In the neutral or rest position, the leaflets' free margins converge to form a non-uniform gap between them. The leaflets have a scallop in their free margins, proving sufficient material at the center to seal against reversed fluid flow with minimum coaptation.

US2004/176658 relates to a medical support net adapted to be placed around an organ; for example a cardiac support net, which is made as a multilayered fabric by a warp knitting technique, preferably from multifilament polyester yarn.

U.S. Pat. No. 4,191,218 discloses woven fabrics for use in vascular prostheses and heart valves, which fabrics are woven from multi-filament (polyester) yarns comprising filaments of about 10 µm diameter, and which fabrics are heat shrunk to result in open interstitial space of 20-40 µm and elongation in at least one direction of at least 10%. The fabrics preferably have a woven selvedge, which forms the free margin of a heart valve leaflet.

In US2005/177227 a method of making a cardiac valve prosthesis is disclosed, wherein a textile membrane, preferably made from polyester or PTFE, is shaped to form leaflets; for example by cutting out segments and using a shaped member reproducing the geometry of a cardiac valve in closed artery position, followed by thermofixation. It is indicated that a leaflet preferably has a woven or knitted free edge to avoid raveling.

US2012/0172978 describes a prosthetic valve comprising leaflets made from an isotropic filter screen material that has uniform pores of 15-60 µm and a thickness of 10-100 µm, and which material is woven from e.g. polyester or polypropylene monofilaments. In response to a closed flow pressure the leaflets can be pushed together to engage at the outflow edge. Methods of making such valve comprise steps of forming separately leaflets from a single layer of said screen material, coupling them together along an attachment line, and optionally coupling to a sewing ring or stent. The attachment line forms a commissure, optionally in combination with connected tabs extending from the ends of the free margin of leaflets at the outflow edge. Typically leaflets are cut from the screen material in such way that the edges of a finished leaflet do not substantially have any extending fibers.

Still there is a continuing need for implantable prosthetic valves having adequate properties for replacing a natural valve, especially showing very good durability.

SUMMARY

The present invention provides a method of making such a prosthetic valve comprising at least one leaflet as defined by the claims. More specifically, the invention relates to a method of making a prosthetic valve (400) that can take a first form wherein the valve is open and a second form wherein the valve is closed, the valve comprising a leaflet (3), a supporting element (2), and a stent (40) to which the leaflet and supporting element are attached, the leaflet having a free margin (5) that can move between a first position wherein the valve takes the first form and a second position wherein the valve takes the second form, the method comprising:
  providing a woven textile structure,
  forming the leaflet and the supporting element from this textile structure, such that a selvedge of the textile structure forms the free margin of the leaflet, and
  forming the valve therewith,
wherein the textile structure has a single layer thickness of between 40 to 150 µm and comprises yarn comprising polymeric filaments, the yarn having a linear density of less than 120 dtex and an elongation at break of 10% or less, and wherein the leaflet is attached to the stent by making stitches through at least 2 layers of the woven textile structure to form a commissure.

In this method thin woven fabric that is substantially made from polymeric multifilament yarn of relatively low thickness or linear density is used for making leaflets and supporting elements, with the free margin of the leaflets being formed from a selvedge of the woven fabric, and the leaflets being attached to the stent by stitching through multiple layers of the woven fabric, to result in durable performance of both leaflets and commissures in actual use. The woven fabric used in the method is thin and flexible, and preferably has high tensile strength and relatively low stretch. Forming the valve may comprise assembling leaflets and supporting elements, and attaching leaflets to the stent with stitches passing through multiple layers of such fabric, to result in a strong and durable commissure at least at the connecting points between adjacent leaflets at the outflow side of the valve, which are typically the places where most stress concentrates during valve opening and closure.

The invention also relates to a prosthetic valve (400) as obtainable by said method, more specifically such prosthetic valve that can take a first form wherein the valve is open and a second form wherein the valve is closed, the valve comprising a leaflet (3), a supporting element (2), and a stent, wherein
  the leaflet has a free margin (5) that can move between a first position wherein the valve takes the first form and a second position wherein the valve takes the second form,
  the leaflet and the supporting element comprise a woven textile structure wherein a selvedge of the woven textile structure forms the free margin of the leaflet,
  the woven textile structure has a layer thickness of 40-150 µm and comprises yarn comprising polymeric filaments, the yarn having a linear density of less than 120 dtex and an elongation at break of 10% or less; and
  the leaflet is attached to the stent by stitches made through at least 2 layers of the woven textile structure.

DEFINITIONS

A prosthetic valve is a constitution of at least one leaflet and supporting element, wherein the leaflet is attached to the supporting element such that the leaflet can flex or hinge to provide an open as well as a closed position for the valve, and may optionally comprise a rigid or semi-rigid support, also called frame or stent.

A leaflet assembly is the combination of at least one leaflet and corresponding supporting element in a generally tubular configuration, and may be made from multiple pieces of material connected together or from one single textile structure (like a woven fabric). The leaflet is the movable part and is attached to the supporting element, also called graft or skirt, and together they define pockets that can be filled with fluid to close the valve.

A commissure is generally a point or line along which two things are joined; in anatomy of natural heart valves a commissure is the distinct area of junction between two adjacent valve leaflets and their supporting vessel wall. Within the present application the commissure refers to the attachment line or region from the outflow side between a leaflet and supporting element in case of a stent-less valve, and between leaflet and stent, and optionally supporting element for a stented valve. In addition to connections forming a commissure, there can be further connections between leaflet, supporting element and/or stent, for example further defining leaflet shape.

A margin of a leaflet is an edge.

Coaptation means abutting, contacting or meeting of a leaflet and a closure surface, such as another leaflet, to close the valve; coaptation height refers to the height or length of coaptation measured from the free margin in longitudinal direction of the valve, i.e. towards the bottom of the leaflet.

The centre line of a leaflet is a hypothetical line from the free margin at the centre of the valve to the nadir at the bottom of the leaflet, that is the lowest point defining the leaflet by connections to the supporting element. In case of a non-symmetrical valve with for example three leaflets, it is the line from the contacting or coaptation point of the three free margins to the nadir.

The curvature height characterizes the curvature in the leaflet of a valve as the largest orthogonal distance between the centre line and a straight line connecting the free margin at the centre of the valve and the nadir.

The radius of curvature of a leaflet is the radius of a circle that best fits a normal section of the curved surface of the leaflet in closed valve position.

An elastic material is a material that is capable of returning to its original shape after being deformed.

To impose a geometry on an object means that the geometry of this object is established by the creation of the object, as opposed to a geometry that can arise due to external forces applied to the object after creation.

Inflow side or bottom side of the valve means the side where fluid enters the valve when it is in open position, the opposite side is referred to as outflow side or top of the valve.

For something to run parallel with another thing means that both things predominantly extend in the same direction.

The elongation at break of a specimen is the elongation of that specimen recorded at the moment of rupture thereof under an applied load, expressed as a percentage of its original length. For sheet material, the elongation at break is often also called elongation at rupture or elongation at fracture.

A yarn is an elongated body having a length much greater than the width of its cross-section, typically comprising a plurality of continuous and/or discontinuous filaments, said filaments being preferably aligned substantially parallel to each other.

Adjacent means adjoining or nearest in position.

A selvedge (or selvage) is an edge of a woven structure wherein the threads that run in a direction perpendicular to the edge of the structure are not extending from the structure as free ends, but are continuous at the edge by returning into the structure. Selvedges are typically formed in fill (also called weft) threads during a shuttle weaving process, but may also be made with other techniques or in warp threads.

BRIEF DESCRIPTION OF DRAWINGS

FIGS. 1A through 1*l* schematically show various steps for forming a valve prosthesis using a method according to the invention.

All figures herein are schematic drawings only and not necessary to scale, and may not show all features or components for clarity reasons. Like reference numbers in different figures refer to like features.

DETAILED DESCRIPTION

Figure 1A:
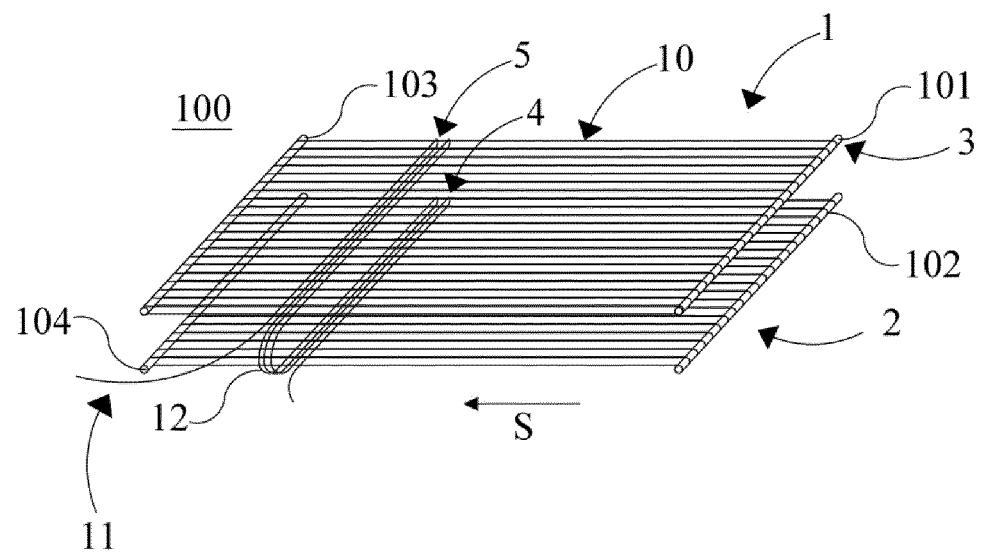

In a first embodiment the method comprises steps of forming a prosthetic valve from a stent, and at least one leaflet and supporting element made from a woven textile structure of layer thickness 40-200 μm and comprising yarn of polymeric filaments, the yarn having a linear density of less than 120 dtex and an elongation at break of 10% or less. Using such thin woven textile structure, herein also called woven fabric, offers more design freedom in making a leaflet assembly than with other materials. Woven fabric made from relatively thin and low elongation yarn provides good flexibility to the prosthetic valve, and allows making stitched connections between fabric and stent using multiple layers. Such multilayer connections are relatively strong and durable and result in good long term performance of the prosthetic valve, yet without unacceptably deteriorating flexibility and movability of the leaflets. A woven fabric further has the advantage over for example a knitted or braided textile structure in that desired properties and shape or form can be incorporated by applying various weaving techniques, and optionally by using various yarns as warp and fill (or weft) threads. The type of weaving pattern is not found to be particularly critical for the woven textile structure to be used in present method, and the skilled person will be able to choose a woven fabric with certain pattern, in combination with its warp and fill threads, to obtain desired properties. Typically, woven fabrics with plain, twill or basket weave patterns are found to provide good performance. For making fabrics having 3D-like shape, especially for making shaped leaflets, also a combination of different weaving patterns may be applied. By using locally a different weaving pattern, for example resulting in a more dense fabric structure, different shapes may result to form e.g. a curved surface as part of the weaving process.

In an embodiment, the woven textile structure comprises a layer having a thickness of between 40 to 150 μm, but layer thickness may be at most 140, 130, 120, 110 or 100 μm and at least 50 or 60 μm for optimal performance, for example between 50 to 100 μm. Such fabrics are strong and flexible to allow free and responsive movement of leaflets, and enable folding into multiple layers to make stronger connections or attachments, especially at a commissure. This layer thickness typically corresponds to a woven textile structure with a plain weave, basket weave or twill weave and with warp and fill threads made for example from UHMWPE multifilament yarn having a linear density of between 5 to 50 dtex. The yarn used in present method preferably has a linear density of less than 60, 50, 40, 30, 20 or even 15 dtex, preferably linear density of at least 5, 7 or 10 dtex; for example a linear density of between 5 and 30 dtex, or between 7 and 15 dtex. Applicant found that there is a major advantage in applying such thin yarns (note: although dtex is not a parameter that denotes actual dimension or spatial length, in practice it corresponds to theoretical yarn diameter as UHMWPE has a density of close to 1 kg/dm$^3$). Particularly, it was found that using such thin yarns in the woven textile structure leads to a fabric that is very flexible, and thus enables fast response of the leaflet under pulsatile load. The flexible leaflets can also easily align with the supporting elements, thus creating a large effective orifice; and also inducing less load on the commissure. Furthermore, it was found that the use of such thin yarns tends to lead to woven textile structures having relatively low pore size, and favourable blood compatibility. Combined with reduced risk of thrombus formation, this will contribute to good bio-compatibility, high effectiveness, as well as durability of the valve during use.

The textile structure used in the method of making a prosthetic valve comprises yarn comprising polymeric filaments and having an elongation at break of 10% or less. Yarns of such low elongation at break often have a relatively high tensile strength or tenacity. Prior art prosthetic valves typically have leaflets that are made from material that allows elastic stretching of about 15%, mimicking stretch properties of natural tissue valves. Against such teaching, applicant found that also woven material made from low stretch yarn can be used for forming valve leaflets, and even provides a more durable valve. Leaflets made from present woven fabrics not only have favourable mechanical properties, but their limited stretching may reduce focal thrombi, other vegetation and collagen growing over the woven during use. Therefore, in embodiments the textile structure is made from yarn having an elongation at break of less than 9, 8, 7, 6 or 5%, preferably between 1 and 5%.

In another embodiment, the woven textile structure comprises ultra-high molecular weight polyethylene (UHMWPE) filaments, preferably at least 80 mass % of UHMWPE filaments having a tenacity of at least 2 GPa, and preferably the warp and/or the fill threads of the woven textile structure consist of UHMWPE filaments. Such UHMWPE multifilament yarns have been found to be ideally suitable for use in weaving a leaflet assembly for a prosthetic valve. The UHMWPE yarns are durable, can be made with the desired mechanical properties and medical grade is available commercially, which medical grade is hardly immunogenic. In particular, it is preferred to use UHMWPE yarn that has an intrinsic viscosity (IV), of at least 5 dl/g, preferably at least 10 dl/g or least 15 dl/g. Preferably, the IV is at most 40 dl/g, more preferably at most 30 dl/g or at most 20 dl/g. IV is determined according to method PTC-179 (Hercules Inc. Rev. Apr. 29, 1982) at 135° C. in decalin, the dissolution time being 16 hours, with DBPC as anti-oxidant in an amount of 2 g/l solution, by extrapolating the viscosity as measured at different concentrations to zero concentration. Particularly preferred are gel-spun UHMWPE multifilament yarns, which typically have a Young's modulus of at least 30 GPa or of at least 50 GPa. Preferably the UHMWPE yarn has a tenacity of at least 2.5 or 3.0 GPa. Tensile properties of UHMWPE yarn are defined and determined at room temperature, i.e., about 20° C., on multifilament yarn as specified in ASTM D885M, using a nominal gauge length of the fibre of 500 mm, a crosshead speed of 50%/min and Instron 2714 clamps, of type "Fibre Grip D5618C". On the basis of the measured stress-strain curve the modulus is determined as the gradient between 0.3 and 1% strain. For calculation of the modulus and strength, the tensile forces measured are divided by the titre, as determined by weighing 10 metres of yarns; values in GPa are calculated assuming a density of 0.97 g/cm$^3$. Preferably the textile structure used in the prosthetic valve comprises at least 90 mass % UHMWPE filaments and most preferably consists essentially of UHMWPE filaments. A preferred example of a UHMWPE yarn is Dyneema Purity® yarn obtainable from DSM, The Netherlands. This type of UHMWPE is particularly preferred since it is a medical grade UHMWPE yarn, the yarns typically having an elongation at break of about 2 to 4%. The ultra-high molecular weight polyethylene may be linear or branched, although preferably linear polyethylene is used due to the very high tenacity and modulus obtainable by stretching during manufacturing of the yarn. Linear polyethylene is herein understood to mean polyethylene with less than 1 side chain per 100 carbon atoms, and preferably with less than 1 side chain per 300 carbon atoms; a side chain or branch generally containing at least 10 carbon atoms. The number of side chains in a UHMWPE sample is determined by FTIR on a 2 mm thick compression moulded film, by quantifying the absorption at 1375 cm using a calibration curve based on NMR measurements (as in e.g. EP0269151).

With the method of the invention a prosthetic valve is made that comprises at least one leaflet. In general valves found in mammals, especially in the blood system, contain one, two or three leaflets; heart valves typically have two or three leaflets. Preferably a prosthetic valve is made that has two or three leaflets, more preferably three leaflets. Making prosthetic valves having more leaflets is likewise possible, but is more complex.

One or more woven textile structures, or pieces of woven textile structure, can be applied for forming leaflets and supporting elements, together also called a leaflet assembly. The method may comprise forming each leaflet and supporting element from separate pieces of woven textile structure and then assembling and connecting the various pieces together; forming multiple leaflets from a one piece of woven textile structure and multiple supporting elements from another piece and then assembling and connecting the pieces together; and forming multiple leaflets and supporting elements from a single woven textile structure. In case of using multiple pieces of woven textile structures, such pieces can be connected to each other, e.g. via a seam by sewing or stitching, before or during attaching them to the stent. For example, a leaflet assembly having three leaflets and corresponding supporting elements may thus be made from 6, 4, 3, 2, or 1 piece(s) of woven fabric. Suitable methods for forming a leaflet assembly from a single woven structure comprise providing a flat woven fabric and folding it, or applying a double weaving technique to make a multilayer fabric, like a so-called double width fabric that is open at one side, or a flattened tubular fabric; as will be further described below.

Forming of leaflets (and supporting elements) from a woven textile structure is done such that a selvedge of the textile structure forms the free margin of the leaflet. A selvedge is a self-finished or self-stabilised edge of a woven textile structure. A selvedge refrains the textile structure from unraveling or fraying at such edge, but -as opposed to other types of stabilised or finished edges—a selvedge is the result of the actual weaving process and not of an additional process step such as cutting, melting, gluing, stitching or other process for providing a stabilised edge. In a woven textile structure, selvedges typically (but not necessarily) run parallel to the warp threads and are created by the fill thread(s) looping back into the set of warp threads after exiting. A selvedge is made inherently in fill threads with a shuttle weaving process, but can also be made in a shuttleless weaving operation by tucking-in the fringed ends of the fill threads after each interlacing and cutting. A further method is introducing additional threads with so-called leno selvedge design in the woven, which will lock outermost thread ends at the edge. By having the selvedge to form the free-margin of the leaflet, this free margin is provided as an inherently mechanically stable edge without using an additional process step. Additional process steps like melting or sewing may complicate the manufacturing process of the valve as a whole, and also may give rise to side effects, like alteration of mechanical properties of the yarns (such as for example increased stiffness, reduced resistance to wear or reduced strength) upon melt fusing of loose yarn ends, or local thickening and reduced flexibility of the fabric after edge stitching. Nevertheless, such additional edge finishing may be suitably used to stabilise edges of a woven textile structure for use in making a prosthetic valve; for example in case of making a continuous or endless woven fabric that later is to be cut into pieces of desired length (also simply called lengths) for forming e.g. leaflets. A suitable example of making a stabilised or finished edge is hot cutting of woven fabric, e.g. with a laser or with an electronic thermal cutter, also called hot knife, which allows simultaneously cutting and fusing fabrics of thermoplastic fibers in a controlled single step. Alternatively, threads with leno design may be included during weaving of the fabric at the places where the fabric is to be cut.

In an embodiment, forming of leaflets (and supporting elements) from a woven textile structure, and forming a valve therewith comprises making a leaflet assembly from one or more textile structures, for example by connecting respective structures by sewing or stitching to form a seam, and subsequently attaching to the stent. In another embodiment steps of forming leaflet or leaflet assembly may at least partly coincide with attaching leaflet and support element to the stent. In the following and in accompanying illustrative Figures this is further explained by making a three leaflet valve as example; but which similarly applies to making other valves.

Reference is now made to FIG. 1, comprising subfigures 1A through 1L, which schematically shows various steps of an embodiment of the method of forming a prosthetic valve. In FIG. 1A a weaving loom 100 is depicted, the loom having four warp beams (or loom bars) 101, 102, 103 and 104. Warp yarns 10 are provided between the upper two warp beams 101 and 103, and between the lower two beams 102 and 104. This way a textile structure having two stacked layers can be formed in one weaving process, using one loom set-up. For reasons of clarity, common other parts of the loom, such as the heald frames (or harnesses) with heddles to separate with a predetermined pattern warp yarns in one layer (or in both layers) to form a clear space (or warp shed) through which (a shuttle or pick carrying) the fill (also called weft) yarn can pass, and the optional bat (or reed) for pushing the fill yarn against the fell of the cloth, are not shown. Warp yarns may be attached to the beams (typical for a dis-continuous process), or may be continuously fed with beams 101 and 102 as guiding members, and 103 and 104 in such case representing a single fabric beam for receiving the two-layer fabric made. The fill yarn 11 as shown in FIG. 1A is woven in the upper layer 3 of the textile structure 1 by interlacing the fill yarn with each of the upper warp yarns (e.g. forming a plain weave), and passes back at the edge 5 of layer 3 towards fold line 12, where it is woven in the lower layer 2 until it reaches edge 4 of this lower layer and then passes back towards fold line 12. Note that for clarity the fold line is made to look larger in the figure than in practice. This way, the edges 5 and 4 are formed as selvedges. The weaving process continues until the textile structure has the desired size. The result is a two layered woven textile structure comprising a first distinct layer 2 having a selvedge 4, and a second distinct layer 3 having a selvedge 5. Layer 2 is connected to layer 3 along the fold line 12, by having fill yarns passing from the one layer to the other. These layers 2 and 3 will form respectively supporting element and leaflets of the ultimate valve, and the fold line 12 may form a part of the connections between supporting element and leaflet. An alternate embodiment further includes interweaving of the layers 2 and 3 by crossing yarns between layers other than at the fold line, to result in further connections and forming e.g. more sections in a layer, partly defining individual leaflets.

Figure 1B:
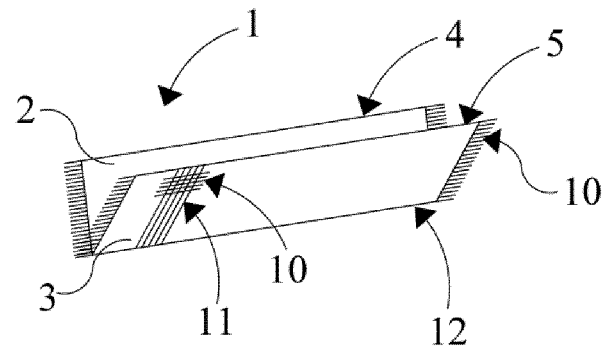

After the textile structure 1 is woven on the loom 100, it is released from the loom. FIG. 1B shows the resulting textile structure that is woven as a double weave (or double width) cloth, having distinct layers 2 and 3, each having a selvedge 4 and 5 respectively. The warp yarns 10 extend over a little length outside of the actual textile structure at the non-selvedge edges. These edges may optionally be stabilised, at this stage or later.

Figure 1C:
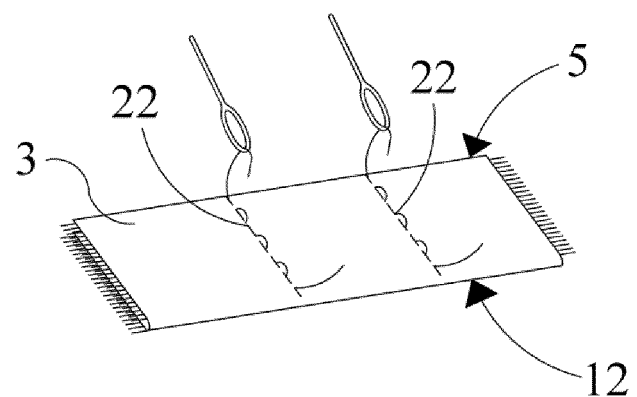

In a next step, as depicted in FIG. 1C, stitches 22 may be added further connecting the layers 3 and 2 (next to fold line 12). By adding two lines of stitches 22 to this structure, layer 3 is divided in three separate sections corresponding to separate leaflets in the valve.

Figure 1D:
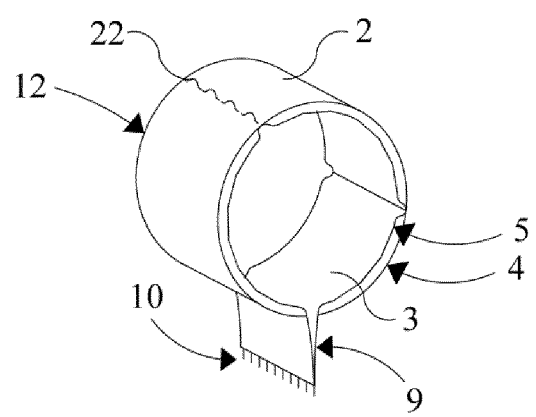
Figure 1E:
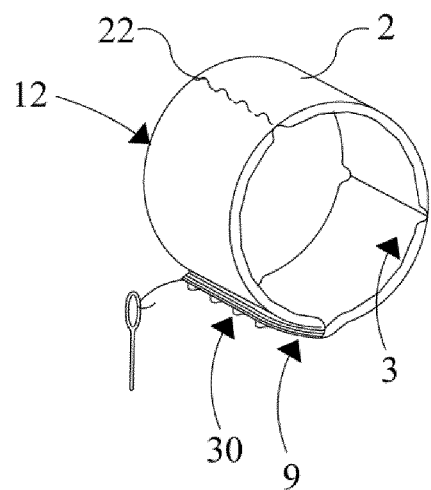

In a next step, as depicted in FIGS. 1D and 1E, the two lateral non-selvedge edges are brought together (i.e. the proximal end and distal end of the structure are configured on top of each other), such that the textile structure forms a tubular structure. As can be seen in FIG. 1D and 1E, the leaflets of layer 3 are situated on the inside, while the supporting elements of layer 2 are situated on the outside of the structure. At the closure 9 of the loop, the warp yarns 10 of both edges of the textile structure meet. Subsequently, the closure 9 of the loop is processed to make sure the closure can withstand the mechanical forces exerted on the prosthetic valve when in use. Firstly the loose warp ends may be cut and then, as can be seen in FIG. 1E, the closure 9 is folded towards the surface of layer 2 and thereafter secured with stitches 30, resulting locally in 4 layers. Alternatively, the folded ends are first rolled up and thereafter folded against layer 2, resulting locally in more than 4 layers. This way, any loose warp yarns ends are no longer freely exposed, but a disadvantage may be that the rolled up closure 9 is somewhat thicker as compared to a non-rolled up closure. A further alternative is to stabilise the edges before connecting to layer 2.

Figure 1F:
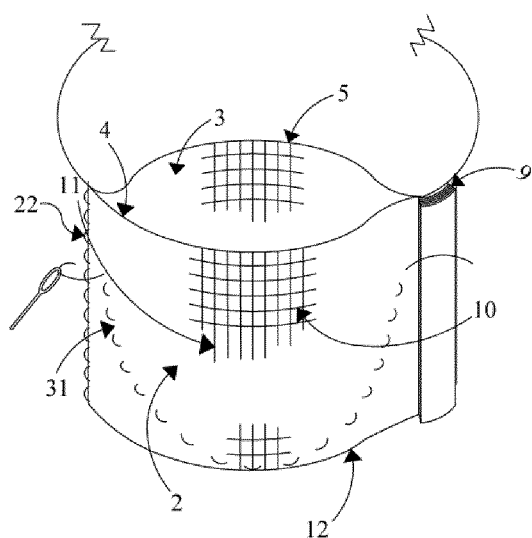

In a another step, as depicted in FIG. 1F, an additional stitch 31 is added, for example following a U-shaped line, which stitch further connects sections of layer 3 and corresponding sections in layer 2, to better define the leaflets or make a 3D-like shape. A segment of the tubular structure showing one combination of supporting element and leaflet is shown in FIG. 1F. As can be seen, the free margin of the leaflet is formed by selvedge 5. The connections made comprise, starting from the free margin, stitch 22 and stitch 31. Stitches 22 and 31 can also be continuous, i.e. stitches 22 may not extend over the full height of the valve, but may deflect and continue forming the U-shaped curve of stitches indicated as 31. This way, the leaflet and supporting element together form a pocket. By taking a position adjacent the supporting elements, the leaflets may open the ultimate valve, and by taking a position that extends away from the supporting elements, the leaflets may close the ultimate valve. These steps can likely be performed in the presence of a stent, also connecting the leaflet by stitches through multiple layers of woven fabric to the stent. For clarity reasons such stent is not shown.

Figure 1G:
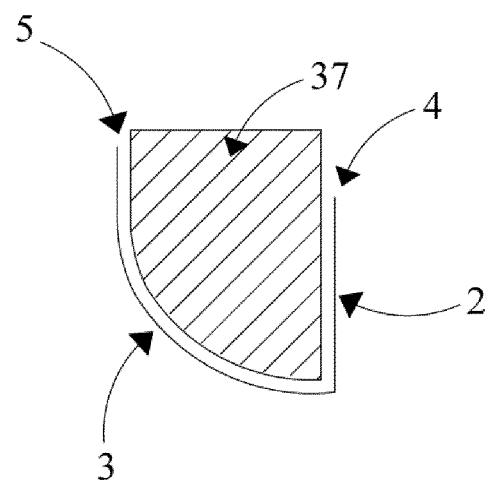

Referring now to FIG. 1G, in order to even better shape the leaflet and pocket, a mould may be used. Before stitching connecting line 31, mould 37 may transpose the leaflet into shape, optionally by pulling the leaflet at edge 5 upwardly. This way, extra length is created between the nadir and the centre of the valve along the leaflet. Another way of creating such extra length is to already weave (sections in) layer 3 to be larger than layer 2, or to have a more 3D-shape; for example by locally within a section changing the weaving pattern or weaving density, or using more warp yarns in layer 3 than in 2. The steps as illustrated by FIGS. 1F and 1G can also be performed during or after connecting to a stent.

Figure 1H:
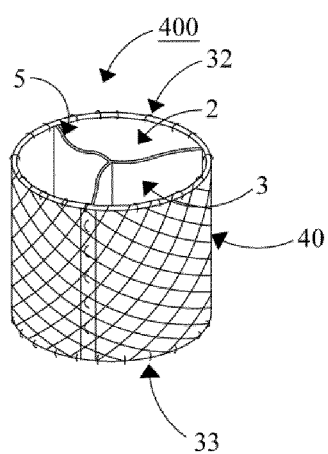
Figure 1I:
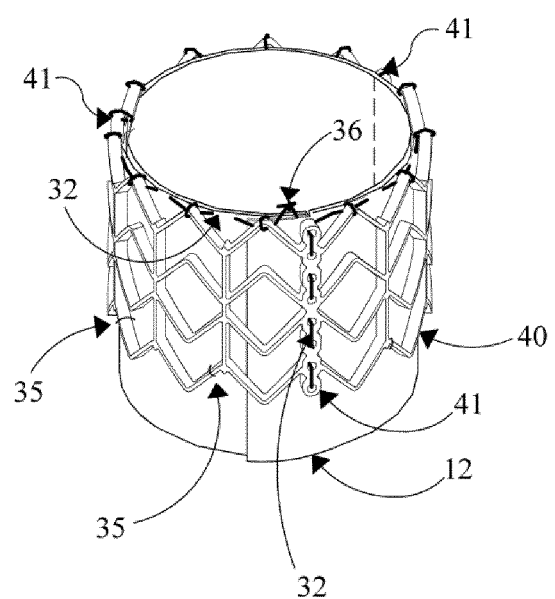

Referring now to FIGS. 1H and 1I, the textile structure or leaflet assembly made is connected to a circular wire stent 40 to make valve 400. The leaflet assembly is placed within the stent and may be connected at its bottom to the stent with stitches 33, and at the top with stitching 32 connecting only supporting elements 2. This stitching 32 preferably continues to connect the leaflets and supporting elements with the three stent posts 41 (see FIG. 1I), such connection further forming the final commissure. The free margins 5 of the three leaflets are also depicted in FIG. 1H. In this form, the valve 400 is closed by coaptation of the leaflets in neutral position. Would the free margins 5 be adjacent the supporting element 2 (i.e. adjacent the wall of stent 40), the valve 400 would be open. Some more details of the stent configuration and its posts 41 are depicted in FIG. 1I. Knot 36 is made in suture 30, as connecting point for suture 32. In an alternative approach, stitches 33 may be made at this stage; then temporary connections 35 may be used to keep the structure in place during suturing to posts 41, and can be removed thereafter. FIG. 1I shows an alternate embodiment wherein the leaflet assembly extends from the bottom of the stent, and this part may in a further step be folded to the outside of the stent and connected thereto. An advantage hereof may be smoother fitting to a vessel or artery upon implantation.

In an alternative embodiment, instead of using stitches 22 early in the forming process (as shown in FIG. 1C), the double woven textile structure as such (as shown in FIG. 1B) is tightly wrapped around the stent 40 (the stent at this stage being covered with a protective sheet of plastic) or another shaping member like a rod, and the four layers of the closure 9 are sutured together. Thereafter the stent is removed carefully, and the tubular textile structure is placed inside the stent. Then, stitches (sutures) corresponding to stitches 31, 32 and 33 are provided in order to form the leaflet cusps and secure the textile structure to the stent.

Figure 2A:
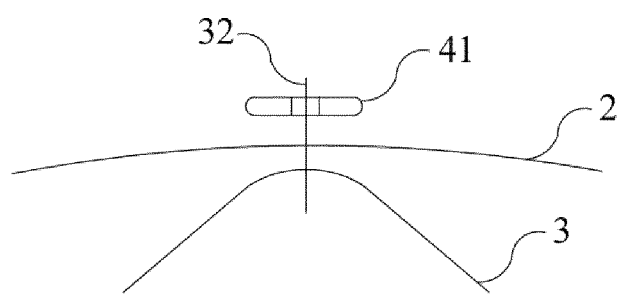
FIGS. 2A through 2E schematically show some arrangements of layers of woven fabric through which stitches are made for attaching to a stent.
Figure 2B:
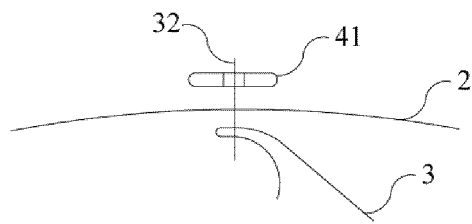
Figure 2C:
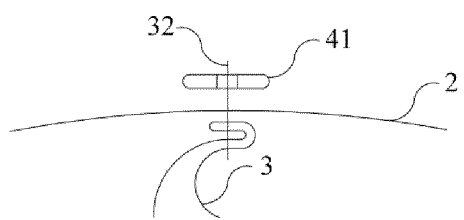
Figure 2D:
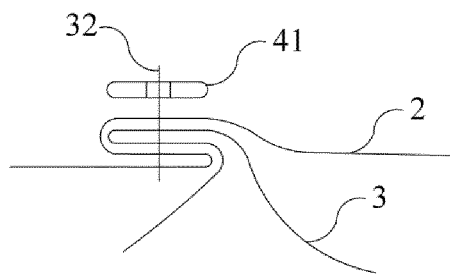
Figure 2E:
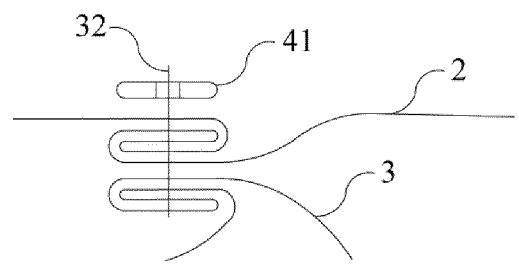
Figure 3A:
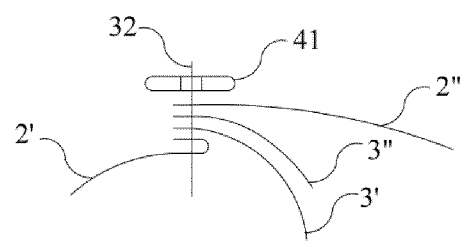
FIGS. 3A through 3C schematically show some arrangements of layers of woven fabric through which stitches are made for connecting pieces of fabric and attaching to a stent.
Figure 3B:
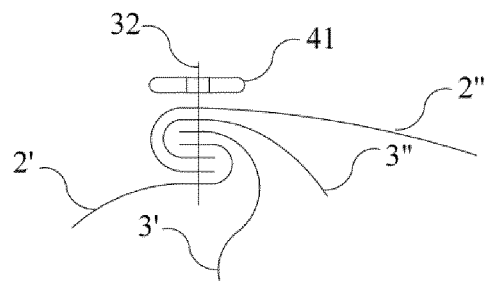
Figure 3C:
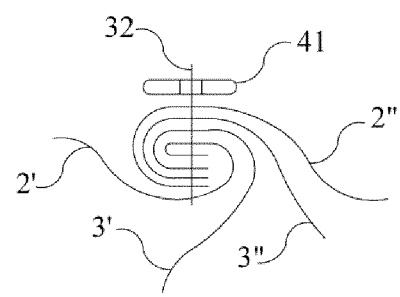

In the above described embodiments the leaflet is attached to the stent by making stitches through 2 or 4 layers of the woven textile structure. As shown as a view from the top or outflow side of the valve in FIG. 2A attaching through 2 layers may result from making a stitch 32 through one leaflet layer 3 and one supporting element layer 2 (and the stent post 41). Attaching of a leaflet to a stent by stitching through multiple layers of leaflet and/or supporting element can be done in various ways, for example by making folds in a leaflet and/or supporting element layer, parallel to the longitudinal axis of the valve. FIGS. 2B-2E show some illustrating and non-limiting embodiments of attaching via 3, 5 or 9 layers of woven fabric. Attaching a leaflet to the stent by stitching through multiple layers of leaflet and/or supporting element can also be combined with connecting ends of several pieces of woven fabric together in forming a leaflet assembly. Some illustrating and non-limiting embodiments are shown in FIG. 3A-3C in a top view as in FIGS. 2, wherein 5, 7 and 9 layers are stitched to connect and attach leaflets 3' and 3".

In an embodiment leaflet and optionally supporting element are attached to the stent by making stitches through at least 3 layers of the woven textile structure, preferably such attachment is made through at least 4, 5, 6, 7 or even more layers to result in even stronger and durable commissures. The thin woven structures used allow making such multilayer areas without significantly deteriorating other valve performance aspects, nevertheless the number of layers is preferably less than 12, 11 or 10. In further embodiments the layers are preferably stitched such that two adjacent leaflet layers 3 (or 3' and 3") can coapt, that is contact each other, virtually to their contacting area in the stitched attachment; see FIGS. 2 and 3; for effective closing of the valve.

In the above described embodiments, the stitched attachment and optionally folds and seam run preferably substantially parallel to the flow direction of the fluid passing the valve, or stated otherwise parallel to the longitudinal axis of the valve; as does the post of the stent to which it as attached, and the commissure. The commissure can also be seen as forming part of the connections between a leaflet and supporting element and/or stent. This commissure may extend over the full height of the stent, that is from outflow side to inflow side of the valve. Typically the stitched commissure has a length of about 5-12 mm, preferably about 7-10 mm; starting from the outflow side. At the outflow side these connections thus form the most critical part of the commissure, but by extending the commissure over such length the stress is not concentrated at one point, as in common designs, but is divided over said length.

Figure 4A:
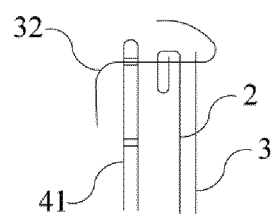
FIGS. 4A through 4C schematically show further arrangements for attaching layers of woven fabric with stitches to a stent.
Figure 4B:
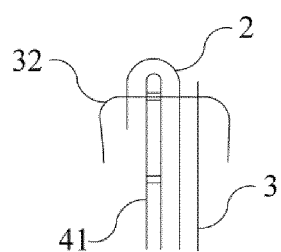
Figure 4C:
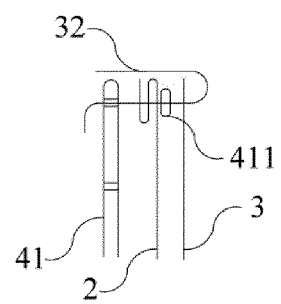

In another embodiment, the method further comprises forming a strong and durable commissure by attaching leaflet and optionally supporting element to the stent by making stitches through layers of woven textile structure, after folding at least one layer substantially orthogonal to the longitudinal axis of the valve, or stated otherwise substantially parallel to the free margins of leaflets. For example, such reinforced commissure can be made by folding the edge of at least the supporting element—and optionally leaflet—at outflow side, optionally over the outflow edge of the stent, and then applying stitches to attach leaflet and supporting element to the stent. In FIGS. 4A-4B examples of such attachment to a stent (post) are schematically shown in side cross sectional view, wherein support layer 3 is folded over 180° before applying stitch 32. FIG. 4C shows yet another embodiment, wherein a patch 411 is placed between supporting element and leaflet. Such patch may also be used at other places, and is preferably made from a piece of woven fabric of UHMWPE yarn.

In an aspect of the method, the stitches to form the commissures are preferably made using a yarn or suture material that has similar strength properties as the yarn of the woven textile structure. In preferred embodiments, stitches are made using a yarn or a suture of suitable size or linear density, which comprises at least 80 or 90 mass % or consists essentially of UHMWPE yarn as defined above to ensure strong and durable commissures.

In an embodiment textile structure(s) for forming leaflets and supporting elements are provided, which structures have such size that after making connections and attachments a generally tubular leaflet assembly results with a circumferential length and diameter of supporting elements at least corresponding to the internal dimensions of the generally circular tubular stent in use (that is after possible expansion upon implantation); whereas the free margins of the leaflets have at least the minimum length needed for closing the valve; i.e. for example the distance between the two ends of the free margin at the commissures via the centre of the valve in case of a substantially cylindrical valve having two or more leaflets. Preferably the free margin of a leaflet has excess length relative to said distance. For example, in case of a substantially cylindrical valve with internal radius R, and having three leaflets of same size that are attached to the supporting element with even distribution between commissures the needed minimum free margin length would be 2R. By making leaflets having at least the same size as the supporting elements their free margin length would be at least $2\pi R/3$; thus creating an oversize factor of at least about 1.05. Still more excess length can be obtained by forming oversized leaflets relative to actual size of the valve or its stent during use.

In general it was found to be advantageous to make a prosthetic valve wherein the leaflet free margins have a total oversize or excess length factor of at least 1.05, 1.07, preferably at least 1.09, 1.11, 1.13 or 1.15, and preferably of at most about 1.4, more preferably at most 1.3, relative to the minimum length needed for closing the valve (for example relative to the minimum length needed to bridge the distance between commissures via the center of the valve). Stated otherwise, the free margins preferably have an excess length of at least 5%, more preferably of at least 7, 10 or 15%, and of at most 40 or 30%. Such excess length of free margins is found to aid in forming a relatively large closure surface between leaflets, that is in a significant coaptation height along the length of the free margins; and thus in effective closing of the valve upon reversed fluid flow and preventing regurgitation.

In an embodiment the prosthetic valve comprises a leaflet that is made such that the leaflet, even without pulsatile load on the valve, can form a coaptation height of more than 0.1 mm along the length of the free margin. Preferably the coaptation height is at least 2, 3, 4 or 5 mm and at most 15, 13, 11, 10, 9, 8, or 7 mm, for example between 3 and 10 mm, preferably between 5 and 7 mm.

In an embodiment of the invention, two flat woven textile structures having two selvedges parallel to the warp direction and of similar or same dimensions are provided. The woven fabrics are placed on top of each other and the respective opposite ends without selvedge (but preferably otherwise stabilised) are made to overlap and then connected to form a circular or tubular structure, by providing stitches through these layers; optionally at the same time attaching them to a stent and forming a commissure and as illustrated in FIG. 3. The inner layer of the tube is further connected to the outer layer, and optionally at the same time to the stent, at similar distances along the circumference relative to the already connected ends (i.e. at about 120° and 240°), by making stitches through these 2 layers of fabric. The method may comprise further steps to form the valve, such as defining and shaping leaflets by using a mould and/or by further connecting leaflet layer and supporting element layer to define for example a U-shaped leaflet or cusp, and attaching the supporting element layer to the stent at the inflow and/or outflow edge thereof.

In another embodiment of the invention, two pieces of flat woven textile structures having two edges with selvedges parallel to the warp direction, and two edges without selvedge are provided, the structure for forming leaflets being longer than the structure for forming supporting elements. The structures are placed on top of each other and the respective opposite ends without selvedge (but preferably otherwise stabilised) are contacted or connected to form a circular or tubular structure. The extending ends are folded onto the outside of the structure, and then stitches are provided through these layers of fabric—see for example FIG. 3—optionally at the same time attaching them to a stent and forming a commissure. The inner layer of the tube now has a larger circumferential length than the outer (supporting element or skirt) layer. Part of this length is used to make two folds in the inner layer parallel to the longitudinal axis and stent posts and at similar distances along the circumference from the already folded/connected ends (i.e. at about 120° and 240°), and stitches are provided through these layers of fabric (for example one supporting element layer, 2 or 4 leaflet layers; see FIG. 2). Alternatively, these last folding and stitching steps can be performed before connecting the ends to form a tubular structure. In another alternate way folds are made in the supporting element layer rather than in leaflet layer, adjusting the dimensions of starting textile structures accordingly. As indicated above, these steps may preferably be combined with attaching leaflets and supporting elements to the stent.

In a further embodiment of the method of the invention, a single piece of woven textile structure is provided for forming leaflet and supporting element, which structure can be made by a double weaving process resulting in a two-layer fabric, for example a so-called double width fabric that has two selvedges at its open side and a continuous fold line at the opposite closed side. In such structure one layer will form supporting elements and the other layer leaflets. The width of a layer is determined a.o. by the number of warp threads, and both layers can be made to have the same or different width or size by varying the respective number of warp threads in each layer. In such weaving process also the leaflet layer can be made to have a larger length than the corresponding supporting element—to create excess length of the free margin in the final valve—by (locally) increasing the number of fill threads in the layer forming the leaflet relative to its supporting element. This way also a shape can be given to the leaflets. In further embodiments connections are made between the layers, which (pre-)define leaflets, either by crossing threads during weaving or providing stiches after weaving.

A double width fabric as described above can be made as a fabric of distinct length in a dis-continuous process, as on a classical loom with warp threads attached to beams, but also in a continuous weaving operation by continuously feeding warp threads to the warp beam. In the latter case a continuous fabric results, which can be cut into pieces of desired length. In both cases the obtained fabric can be made into a tubular structure by connecting the fabric edges with warp (or cut) ends together, wherein supporting elements will form the outside and leaflets are on the inside of the structure. The warp threads in these embodiments run parallel to the free margin, which is a selvedge of the fabric (similarly for top edge of supporting elements). Attaching through multiple layers to a stent can be done analogously to above embodiments.

Figure 5A:
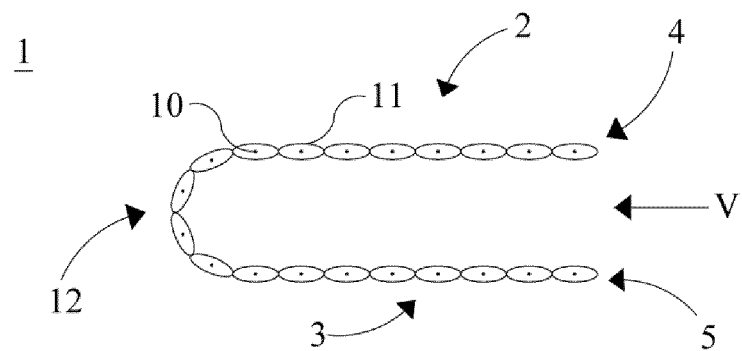
FIGS. 5A through 5C schematically show various views of a woven textile structure suitable for making a valve prosthesis.
Figure 5B:
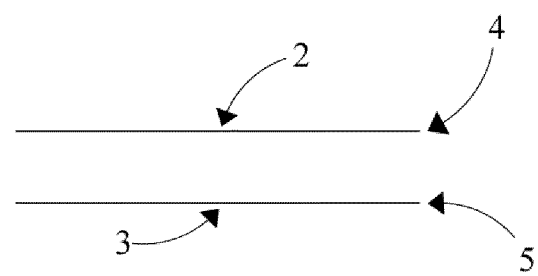
Figure 5C:
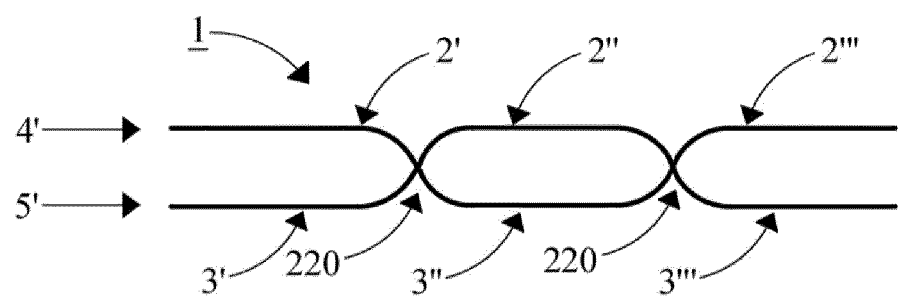

Referring now to FIG. 5, sub-figures 5A, 5B and 5C schematically show various views of a textile structure suitable for making a prosthetic valve. In the embodiment of FIG. 5A, a cross section parallel to the fill yarn of the textile structure 1 in the direction S, as shown in FIG. 1A, is shown. As can be seen, the fill yarn 11 is interlaced in layers 2 and 3 with warp yarns 10 to form a plain weave. By using the double weave method as depicted in FIG. 1, both layers 2 and 3 have longitudinal (i.e. parallel to the warp yarns) selvedges 4 and 5 respectively. The fill yarn, at fold line 12 passes from layer 2 to layer 3 and vice versa, thereby forming part of the ultimate connections between leaflet and supporting element. In FIG. 5B, a side view of this textile structure in the direction V as indicated in FIG. 5A is given. In this view, only the selvedges 4 and 5 are schematically depicted.

In an alternative embodiment, as depicted in FIG. 5C and representing a similar viewpoint as in FIG. 5B, the fill yarn is interlaced with the warp yarns in such way that cross lines 220 are formed in the textile structure. The textile structure 1 now comprises in total 6 sections in the two layers, viz. sections 2', 2" and 2'" in the top layer and sections 3', 3" and 3'" in the bottom layer. At the left cross line 220, the four sections 2', 2", 3' and 3" coincide along a line that will correspond to part of the commissure of the ultimate valve. For this, warp yarns pass from section 2' to section 3" and warp yarns pass from section 3' to section 2", as controlled during weaving by the moving pattern of heddles and warp yarns. This way not only a mutual configuration is obtained wherein each section corresponds with a supporting element or leaflet, but also, a leaflet-supporting element connection is formed as a direct result of the weaving process, and has similar strength as the fabric itself. This also means that less stitches need to be added to form the ultimate commissure, including attaching to a stent. A corresponding weaving process takes place at the right hand cross line 220. By connecting the ends of the structure obtained as depicted in FIG. 5C a tubular three-leaflet structure is obtained.

Figure 6A:
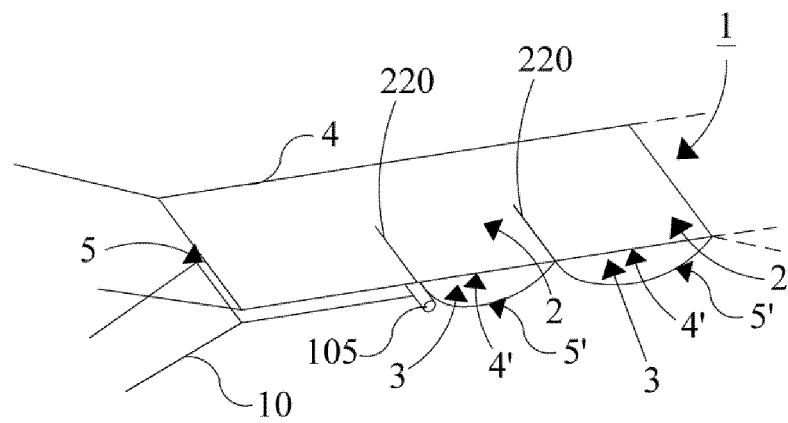
FIGS. 6A and 6B schematically show some steps in another embodiment of the invention.
Figure 6B:
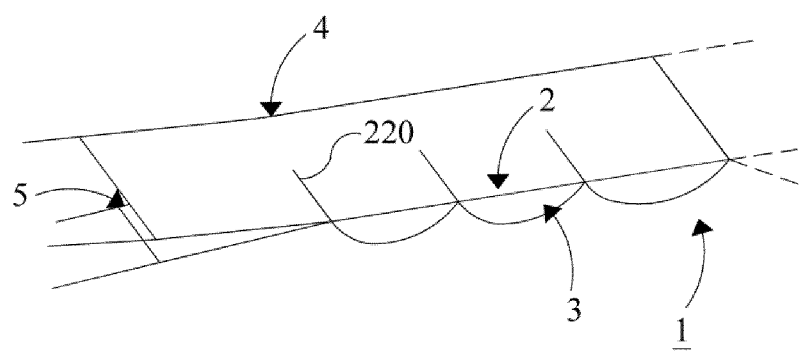

FIG. 6, consisting of sub-figures 6A and 6B, schematically shows a continuous structure produced according to another embodiment, in line with the method as described in conjunction with FIG. 5C. In this embodiment a textile structure 1 is woven with two fill yarns, one for each layer, so that the top and bottom layers 2 and 3 have a selvedge at both sides (4, 4', 5 and 5'). Layer 2 is larger in width direction than layer 3 by using more warp yarns; note that only at the edges warp yarns 10 are depicted for both layers. In the resulting leaflet assembly the supporting element will thus be longer and extend away from the leaflets; and thus can be used for example to fold around a stent. The selvedges 5' may form the free margin of the leaflets in the resulting valve.

The bottom layer is at least locally further extended with extra fill yarns to increase the size of the leaflet and create excess length in the free margin. When the desired extra length for the leaflets is reached, layer 3 is pulled back with retaining bar 105 so that the fill line of the top layer is in line with the bottom layer as shown in FIG. 6A. The warp yarns of the bottom layer and the corresponding part of the warp yarns of the top layer are than crossed to form cross line 220; also shown in FIG. 6B. These cross lines provide that a connection at least for the length formed by cross lines 220, starting at the free margin runs in parallel with the longitudinal axis in the ultimate valve formed out of structure 1 (corresponding to the method as outlined in FIG. 1). After weaving, the product may be cut into desired lengths, connected to form a tubular structure, and attached to a stent as described above (the connection made may then form part of the commissure).

Alternatively, leaflets may be made to be larger than supporting elements. In a further alternative way, a fold line is formed at one edge by crossing fill yarn to the other set of warp yarns.

In another embodiment, a woven textile structure is made by a double weaving process that results in a seamless tubular fabric, also called flattened tubular fabric, flat-woven tubular fabric or hollow elongate fabric; as it results from a continuous fill thread crossing over from one set of warp threads forming a first layer to the other set forming another layer at each side edge after every interlacing. It is noted that in such case an uneven total number of warp threads is used to omit weaving errors, typically referred to as 'error corrected tubular weaving' in the art.

In an alternative embodiment, a tubular woven fabric is made by using an endless warp beam, like a circular or triangular beam. Further, in addition to a one tube or one channel structure, also multi-channel or multi-layer tubular woven fabrics can be made by using multiple sets of warp threads and beams, specific designs of endless beams (that is beams having ends joined, like a circular loop), and/or specific crossing patterns of threads between the layers or tubular structures.

As also described above, tubular fabrics can be made in a continuous weaving process or in a dis-continuous weaving operation. In an embodiment the method comprises continuous weaving, and the resulting endless (multi-) tubular woven fabric is subsequently cut into desired lengths. One of the cut ends of the tube will form the free margins of leaflets, but since warp threads running lengthwise in the tube will after cutting extend from the fabric edge, a finishing step to stabilize the cut end is applied. Various stabilising methods can be used for both ends of the tubular structure, preferably a thermal treatment is applied to a woven fabric made from thermoplastic polymer fibers. More preferably cutting and stabilising is combined by using a hot knife or other thermal method. After finishing the cut edges, the tube may be partly inverted; i.e. part of the tube will form a tube within the tube and the outside will form the supporting element layer and inside the leaflet layer. By making connections between the layers two or more valve leaflets and corresponding supporting elements can be made, optionally combined with attaching the tubular structure to a stent. Steps in such methods are for a greater part analogous to those shown in FIG. 1.

In another embodiment a tubular woven fabric is made piece-by-piece by a dis-continuous weaving process. In this way a selvedge can be woven in the warp threads, by not connecting the warp threads directly to the warp beam but via additional threads and/or hooks; for example using the Navajo or warp selvedge system as known in the art.

In an exemplary embodiment a substantially cylindrical single-channel tube is woven, ends are optionally stabilised, and subsequently the tube is partly inverted to make a tube within the tube. Inner and outer layers having the same diameter, the free margins of the leaflets will in this case be of substantially the same length as the corresponding supporting elements; thus having an excess length of about 5%. In a further embodiment a tapered or conical tube is made, preferably by using a weaving process including gradual changes in number of warp threads in the woven fabric resulting in gradual changes in diameter—tapering—in the tube as for example described in U.S. Pat. No. 5,800,514 or US2014/0135906. A length of tubular woven fabric having a first diameter at one end that is larger, preferably at least 2 or 5% larger, than the second diameter at the opposite end and with a gradual transfer of first to second diameter is provided, and the ends are optionally stabilized. Then the tube is partly inverted such that the formed inner layer has a larger diameter than the outer tube; meaning the free margins of the leaflets will have an excess length of more than 5%. In further embodiments, multilayer tubular woven structures, as described in drawings hereafter, can be processed in analogous ways to form a leaflet assembly for use in the method of the invention.

Figure 7:
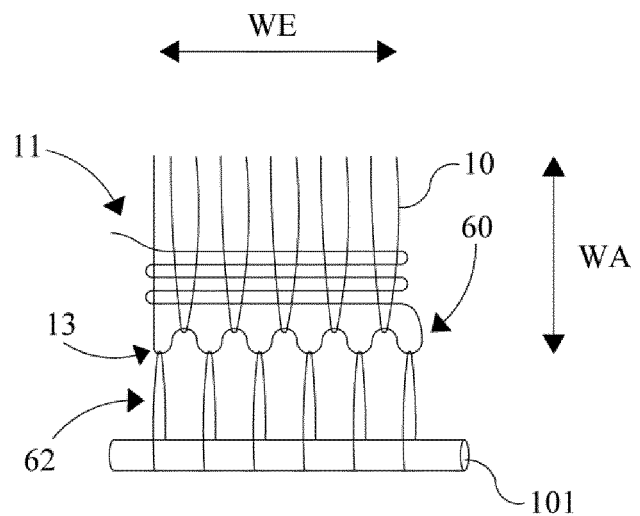
FIG. 7 schematically shows how a selvedge can be woven in an edge perpendicular to the warp direction.

FIG. 7 schematically shows how a selvedge can be woven in an edge perpendicular to the warp direction WA. In this case, connected to the warp beam 101 is a stay, comprising multiple hooks 62. The warp yarns 10 each form a loop, and each of these loops is connected to the beam using the hooks of the stay, which thus extends between the warp beam 101 and the said loops. The fill yarn 11 is interlaced with the warp yarns 10 in fill direction WE. In this particular embodiment a cord 60 is used to fix the said loops to the hooks 62. For this, the cord 60 extends along the margin 13 through each loop of the warp yarns, and is connected to the warp beam using the stay as indicated here above. In this case, the cord 60 is a section of a warp yarn and further continues as the fill yarn 11, so there are no loose ends in edge 13.

Using this method the warp yarns at the margin 13 form a loop, and thus are continuous at this margin forming a selvedge. The resulting flat fabric has thus at least selvedges at three of its edges. This way of forming a selvedge in warp threads can also suitably be used in forming non-flat but e.g. tubular textile structures, wherein this edge or margin corresponds to the free margin of a leaflet upon forming the ultimate valve. Examples of such tubular textile structures are schematically depicted in the following figures.

In another embodiment, the hooks connect the warp beam directly to loops of the warp yarns. To prevent a free end of the fill yarn, it is preferred to loop the fill yarn around one of the warp yarns (advantageously a yarn near a side of the weave if the weave is a flat weave) and thereafter weave using the two ends of the fill yarn as individual fill yarns.

It was found that use of UHMWPE yarns as fill yarn was particularly advantageous when preparing a woven fabric with a selvedge parallel to the fill yarns as the yarns tended to adjust transversely, to fill the loops of the warp yarn when stay or hooks were removed. It could be theorised (without wishing to be limited thereto) that this surprising finding for a yarn with very high strength and modulus, is related to the combination of the low friction coefficient of UHMWPE and bending flexibility of UHMWPE yarns.

FIG. 8, consisting of sub-figures 8A through 8F, schematically shows various steps of another embodiment, in which method a tubular (endless) woven textile structure is used for making a leaflet assembly for a prosthetic valve.

Figure 8A:
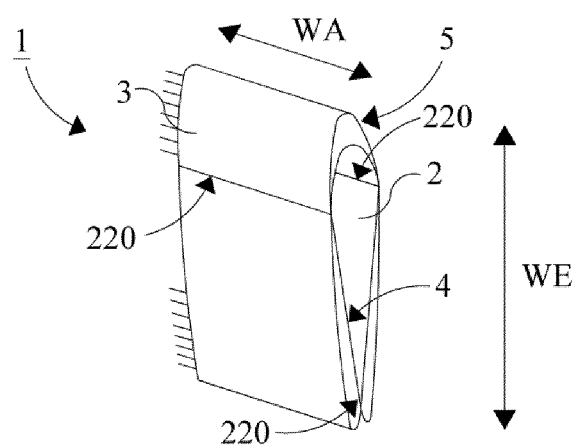
FIGS. 8A through 8F schematically show views of a woven textile structure in another embodiment of the invention.
Figure 8B:
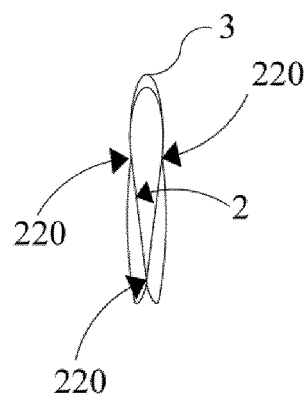
Figure 8C:
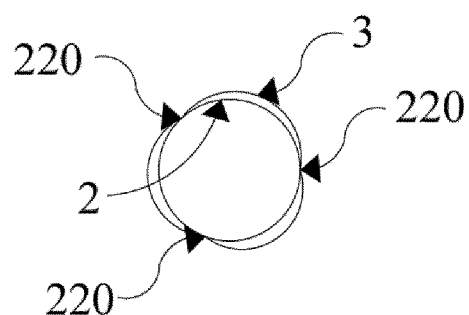
Figure 8D:
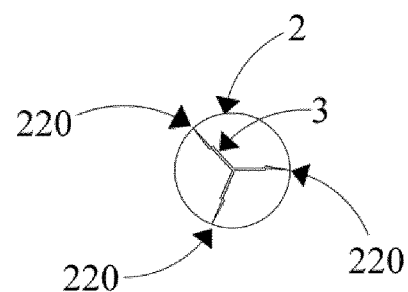
Figure 8E:
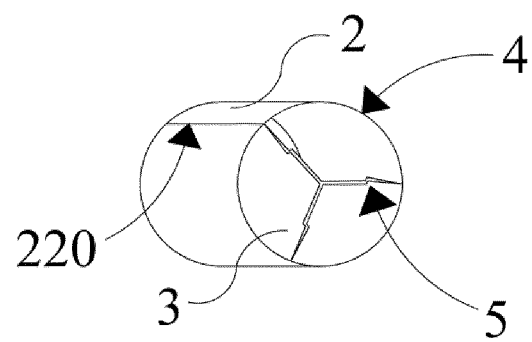

FIG. 8A (warp direction is indicated as "WA", fill direction as "WE") shows a tube-like woven textile structure 1 consisting of inner tubular layer 2, having three sections corresponding to supporting elements of the leaflet assembly as depicted in FIG. 8E, and outer layer 3 having three sections, which will correspond to leaflets having excess length in the free margins. The outer and inner tube are connected along three lines 220. In this embodiment the inner tubular layer 2 has selvedges 4 and the outer layer 3 has selvedges 5, a textile structure resulting from e.g. the method described in FIG. 7 using a warp beam of specific design. Such structure may also be made in a continuous weaving process, followed by cutting to desired lengths and making stabilised edges. The leaflet sections in layer 3 are connected to the supporting elements in layer 2 via cross lines 220 (corresponding to cross lines 220 as depicted in FIG. 5C, albeit that in this case the fill yarns cross, whereas in FIG. 5C the warp yarns cross).

FIG. 8B gives a top view (or cross sectional view) of the textile structure of FIG. 8A (in warp direction) as made. FIG. 8C presents the same view, but with the textile structure from its original flattened form now being configured such that layer 2 forms a circular tube. The leaflet sections of layer 3 extend over the surface of this tube and meet at the cross lines 220. In a next process step the textile structure of FIG. 8C is turned inside out, which leads to a structure as depicted in FIG. 8D. At this stage, the textile structure is processed such that the supporting elements 2 are on the outside, and the leaflets 3 are on the inside, thus forming a leaflet assembly or valve 400 as shown in FIG. 8E in an isometric view (in closed valve configuration).

Figure 8F:
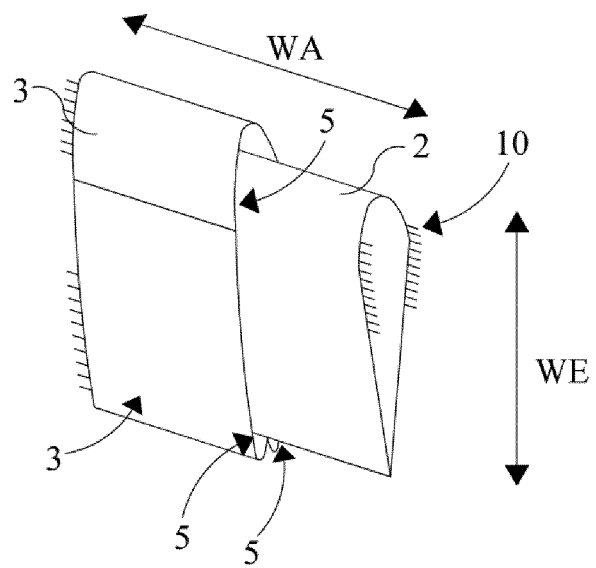

In FIG. 8F an alternative embodiment of a textile structure using a method similar to that described above is schematically depicted, in which embodiment layer 2, unlike the structure as shown in FIG. 8A, extends over a longer distance than the layer 3. In this embodiment, the margin 5 of the leaflet section(s) in layer 3 is formed as a selvedge (for example using a circular warp beam and using a method as depicted in FIG. 7), and the margin of layer 2 is woven as a regular edge wherein the warp yarns are discontinuous at the edge (for example discontinuous since they are cut to release the structure from the loom). For simplicity only some ends of warp yarns 10 are depicted, similarly to FIG. 6A. This textile structure can be formed into a leaflet assembly for a valve the same way as the structure of FIG. 8A, that is by inverting. An advantage of the resulting leaflet assembly is that the supporting element is longer, extending away from the actual leaflets, and thus can be used for example to connect to the outside of a stent used in making a prosthetic valve or to attach the leaflet assembly to a vessel or an artery as a valved graft to (partly) replace a weak or damaged vessel. Similarly layer 2 may extend at the opposite end of the structure, or layer 3 may be made larger. The leaflet assemblies made according to the described method can be attached to a stent analogously to the steps described herein above.

Figure 9A:
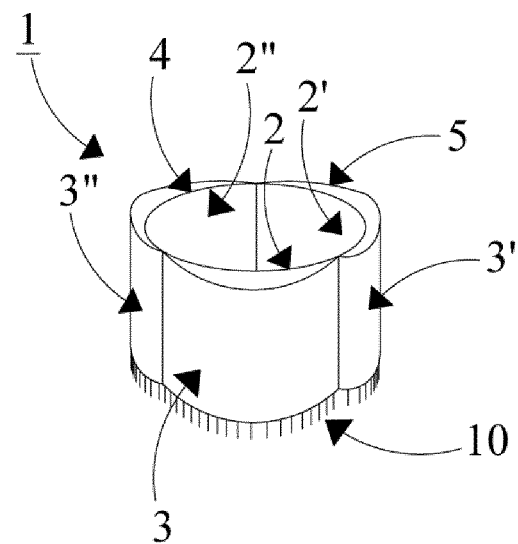
FIGS. 9A through 9D schematically show various steps in yet another embodiment of the invention.
Figure 9B:
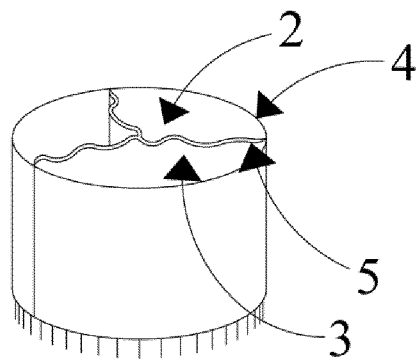
Figure 9C:
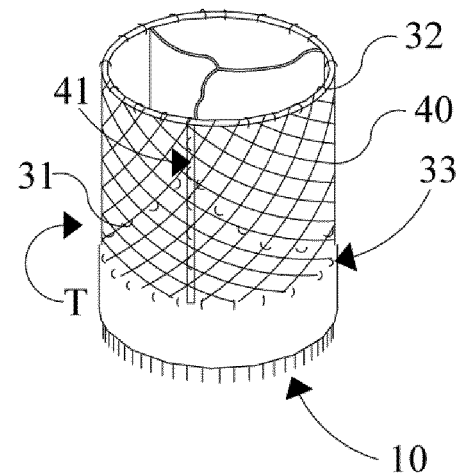
Figure 9D:
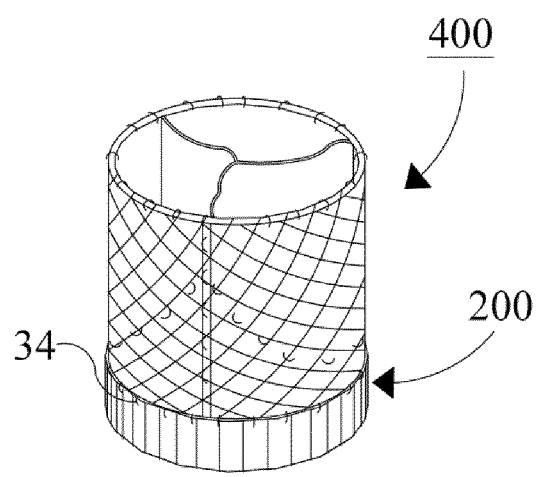

FIG. 9 schematically shows in sub-figures 9A-9D various steps in yet another embodiment of a method according to the invention, corresponding in large to the method of FIG. 8. A multilayer tubular woven structure has is shown, wherein at the bottom side warp yarns 10 are discontinuous after releasing the textile structure from the loom, as depicted in FIGS. 9A (the structure as woven and released) and 9B (the inverted structure). In this embodiment a stent 40 is used to attach the inverted structure of FIG. 9B to, as shown in FIG. 9C. Stitches 31, 32 and 33 are added, corresponding to the stitches as shown in FIGS. 1F and 1H. Lastly, the free end of the textile structure, which extends from the inflow side of the stent, is turned around the stent as indicated in FIG. 9C with the arrow T. As can be seen in FIG. 9D, this way a rim 200 is formed by connecting the textile structure to the stent with stitching 34. The rim can function as a cushioning layer, or be used to suture the valve to the artery or aorta opening.

In another embodiment forming the leaflet may further comprise shaping the leaflet by contacting with a mould of desired shape, optionally heating the mould to a temperature of 3-60° C. (preferably 5-40° C.) below the melting point of the UHMWPE (see ISO11357-3 for a determination of the melting point of a polymer), optionally creep forming the textile structure (i.e. altering its dimensions), and submitting it to a controlled relaxation and/or plastic stretching to conform to at least a part of the mould. Such thermal forming process is for example described in WO2010/020660. With this embodiment the geometry of the leaflet can be further fine-tuned, for example to create certain curvature or to meet certain clinical demands.

In another embodiment a geometry is imposed to the leaflet such that it has a convex surface, relative to fluid entering at the bottom of the valve, with a radius of curvature at the centre line of the leaflet of between 1 and 20 mm, for example 1, 2, 3, 4, 5, 6, 7, 8, 9, 10, 11, 12, 13, 14, 15, 16, 17, 18, 19 or 20 mm, preferably about 12 mm. It is believed that an imposed convex geometry with this particular small radius, as opposed to typical radii in known prosthetic valves of 50 mm or above, leads to less stress and deformation in the leaflet material and possibly less tension on the commissures. Such geometry also results in pockets defined by leaflet and supporting element with relatively large volume, which will be filled with fluid during closing. This may also promote effective re-emptying upon opening, preventing e.g. blood remaining in a pocket and reducing risk of thrombus formation.

Figure 10A:
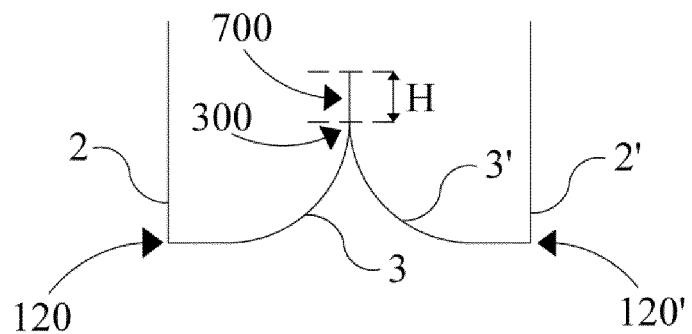
FIGS. 10A and 10B schematically show a cross section of a two-leaflet valve with coapting leaflets.
Figure 10B:
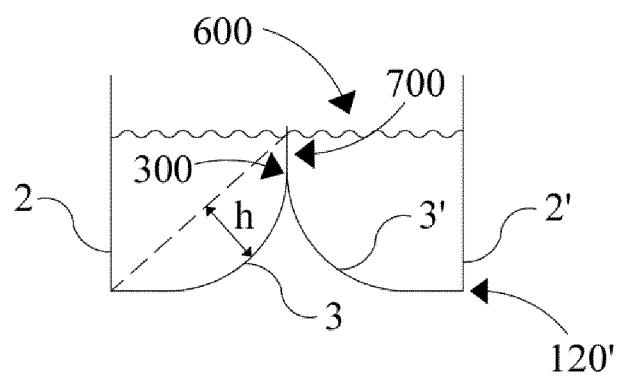

In FIG. 10A a cross section of a leaflet assembly having two opposing leaflets in a prosthetic valve is shown. The leaflets 3 and 3' have a geometry in neutral position without pulsatile load that enables them abut each other along the length of the free margin, thus also at the centre of the valve, and therewith form a coaptation 700 with a coaptation height H at this cross section. The coaptation height H in this embodiment extends with a minimum of 0.1 mm (the bottom of which is indicated with reference number 300) over the length of the free margin of each of the leaflets, possibly becoming even larger towards the commissures depending on commissure length. The geometry also comprises per leaflet a convex surface that extends between the top of the closure surface H and the respective connections to supporting elements, of which nadirs 120 and 120' are indicated. Each convex surface bulges away from the respective supporting elements 2 and 2'. In FIG. 10B it is shown that by a slight hydrostatic pressure, for example created by filling the pockets with water 600 as indicated, the imposed geometry and the coaptation height including formation of a closure "ribbon" having the length of the free margins can be inspected more easily and its dimensions estimated. It is noted that due to excess length of the free margin (more textile length then actually needed to span the distance between supporting elements and to coapt), it might be that at some spots when closing the valve by filling it with water, there is a wrinkle or small opening (a channel) in the closure surface. Such opening however is not persistent and will be closed in actual use by pulsatile. Height h is the largest orthogonal distance between the line section connecting free margin and nadir, and the curved surface of the leaflet.

In another embodiment the leaflet comprises a convex surface, wherein the curvature height h at the centre line of the leaflet is more than 1 mm, preferably more than 2, 3 or 4 mm most preferably about 5 mm. A maximum value is inherently dependent on the outer dimensions of the valve itself, but is typically about 10-15 mm, for example 10, 11, 12, 13, 14, or 15 mm. It is believed that an imposed convex geometry with this particular shape, as opposed to typical curvature heights between 0 and 1 mm for prior art valves, leads to less stress in the leaflet material and possibly less tension on the commissures.

In yet another embodiment the method further comprises steps of decreasing the permeability of the woven textile structure by applying a coating or optionally arranging the structure in a mould, heating to a temperature of 3-15° C. below the melting point of the UHMWPE, and holding at a temperature of 3-15° C. below the melting point for 10 seconds to 2 hours to impart a partial connection between adjacent filaments and/or yarns in the textile. Depending a.o. on the cross section of the yarns and their arrangement in the textile structure (for example type of weave), it can be advantageous to decrease the permeability of the textile structure.

In the method of the invention a prosthetic valve is made comprising a stent. Such stent or frame is a rigid or semi-rigid structure typically comprising a rigid member, and often is of ring or cylindrical shape. Suitable materials for making a stent include rigid polymers, fiber-reinforced polymers, metals and their alloys, ceramics and combinations thereof. Suitable rigid polymers include polyacetals, dextroplast, polyurethane, polyethylene, polysulfones, polyethersulfones, polyarylsulfones, polyetheretherketones, and polyetherimides. Suitable metals include biocompatible metals, such as, stainless steel, titanium, cobalt alloys, such as Elgiloy®, a cobalt-chromium-nickel alloy, and MP35N, a nickel-cobalt- chromium-molybdenum alloy, and Nitinol®, a nickel-titanium alloy. In addition, stents can be produced from ceramic materials, such as pyrolytic carbon, silicon carbides or metal carbides, hydroxyapatite and alumina. Suitable stents can also be produced from carbons such as graphite. Preferably, a stent is at least partly made from a super elastic alloy, or a shape memory alloy, such as Nitinol®, that is available as a super elastic material, as well as a shape memory alloy. Such a stent allows to easily insert the valve prosthesis into the body in a desired position. Before insertion, the self-expandable stent is brought to a first (relatively low) temperature at which it has a compact configuration. This compact configuration allows to easily insert the stent (and the valve in conjunction therewith) into the body, using minimal invasive surgery. After positioning the stent, the shape memory alloy will heat up to the body temperature and change phase, thereby changing its shape into a larger diameter. For Nitinol® for instance, a phase change will occur between an austenitic phase and a martensitic phase. As a result the stent will expand and thereby create a clamping force against surrounding tissue. In another configuration, Nitinol® is super elastic and can be elastically deformed up to material strains of about 10%, thus deformation of a valve towards a compact shape is possible, still allowing elastic deployment to the final shape after placement.

The invention also relates to a prosthetic valve obtainable with or obtained by the above described methods, more specifically such prosthetic valve as defined in the embodiments listed below and by the claims.

The invention will now be further illustrated using the following non-limiting experiments.

EXAMPLE 1

This example describes making a prosthetic valve according to the invention, and experiments wherein such valve is tested in vitro and used as apulmonary valve prosthesis by implanting in sheep. In this example, each valve is made with the method described below, which is basically corresponding to the method as described in connection with FIG. 1 and FIG. 3B.

A woven fabric as shown in FIG. 1B was made from Dyneema Purity® TG 10 dtex UHMWPE multifilament yarn (available from DSM, The Netherlands) with a density of 458 warp yarns per inch and 223 fill yarns per inch. The folded two-layer structure had a length of 90 mm and a width of 21.5 mm, a layer thickness of 0.00314 inches (80 µm), and was woven as a 2 by 2 twill weave, with longitudinal selvedges. The cylindrical stent used has the design as shown in FIG. 1I, and was made of electromagnetically polished stainless steel 304. It had an outer diameter of 25 mm, an inner diameter of 23 mm and a height of 17 mm. For the stitches, two kinds of suture thread was used: Maxbraid PE 3-0 suture blue with tapered needles (available as MPC 900252 from BIOMET MERCK LTD), here beneath referred to as Suture A, and Maxbraid PE 4-0 suture blue with tapered needles (available as MPC 900244 from the same supplier), here beneath referred to as Suture B. Both sutures comprise UHMWPE yarn.

The pulmonary valve was made as follows. In order to create a coaptation height of 6 mm over the length of the free margins of the leaflets, extensive free margin length was created. The free margin length was oversized by following steps:

1. The leaflet free margin length in the textile structure as woven will be inherently equal to the supporting element length, the two layers having the same length. The distance between the edge of the supporting element formed as a cylinder and the middle of the valve being its radius R, the total length needed for 3 leaflets bridging this distance is 6R, whereas the length of the supporting element is $2\pi R$. This creates an inherent excess length factor for the leaflet of $2\pi R/6R=1.05$.
2. The two layer woven fabric is initially wrapped around (i.e. to the outside of) the 25 mm stent and the ends perpendicular to the free margin of the leaflets are sutured together. Subsequently the cylindrical textile structure is placed inside the stent of inner diameter 23 mm and fixed to the stent with UHMWPE sutures. This creates an excess length factor of $25/23=1.09$.
3. In this example the final prosthetic heart valve size is 23 mm for implantation, therefore the stent of 25 mm outer diameter is radially compressed to 23 mm. This way the inside diameter of the stent where the supporting element and leaflet is fixed to is reduced from 23 mm to 21 mm. This creates an excess length factor of $23/21=1.10$.

The total excess length factor of leaflet free margins created this way is $\pi \times 25/3 \times 21=1.25$. The excess length thus created is about 25%.

As indicated here above, the woven fabric is tightly wrapped around the stent, initially being used as mold, and the four layers at the closure (corresponding to 9 in FIG. 1D) are sutured together with Suture A starting at the outflow side of the fabric/stent combination by creating a knot 36, leaving about 2 cm loose end and a long end which is used to create a stitch line towards the inlet side of the fabric/valve combination. The stent/mold is removed carefully, and the tubular textile structure is placed inside the stent. The orientation of the warps of the leaflets and supporting element are perpendicular to the longitudinal central axis of the stent and commissural stent posts, ergo the fill yarns are in parallel to the central axis and commissural stent posts. The Suture A is then guided across fringe and stent post holes from inlet side towards outlet side (as shown in FIG. 1I), thus fixing the stent post 41 to the folded layers of supporting element and leaflet at a length of about 9 mm. At the top of the post (outflow side) suture A is used to fix the edge of the supporting element to the stent in a continuous way by taking locked bites at the bended ends of the stent (the commonly known "Method of Blalock" using a festooning suture line). The end of the suture A is tied to its beginning at knot's 36 loose end. The textile structure is temporarily fixed to the remaining commissural stent posts 41 in a 120 degree fashion thus dividing it in three parts with about the same free margin length, to keep the structure in place during next steps; after which the temporary fixations can be removed.

A second suture B is used to complete attaching of the textile structure and create the actual leaflet assembly within the stent, by stitching to the two remaining stent posts 41 through the two layers of support element and leaflet with a length of about 9 mm, and by stitching leaflet layer to the supporting element layer and stent to create the valve cusps. Prior to suturing, the free margin of all three individual leaflets were pulled up 3 mm in the middle of the free margin at the expense of length of the supporting element at the inflow side thus creating an arch of woven fabric between commissural posts elevated over the plane of the stent outflow side. Together with the aforementioned excess length this results in about 6 mm coaptation height in the center of the heart valve, and is likely even higher towards the commissures of about 9 mm. A mold (a negative form taken from a human aortic valve) is used for further sizing and shaping the belly of the leaflet as shown in FIG. 1G. The leaflet assembly is temporarily sutured (35) in the middle between the posts at the inflow side to maintain this configuration during next step. From this point suturing is started according to FIG. 1I. At the top of the post the leaflet and supporting element are taken double with two encircling bites. The leaflet sheet is pulled a little bit backwards over the top of the stent and is fixed by the suture. The course of the suture line of the leaflets (U-shaped) is also guided by the shapes of the stent and mold. The end of the suture is tied to the loose end left at the knot of the beginning of suture B. The resulting leaflets had a convex surface at the centre line of these leaflets with a radius of curvature of about 12 mm without pulsatile load. This was estimated to represent a distance h as depicted in FIG. 3C along the centre line with a height h of about 5 mm. The textile structure extends a few millimetre from the stent at the inflow site, as also shown in FIG. 1I, which can be used to attach the valve to vessel or artery wall upon implantation. The leaflet assembly is further connected with sutures to the lower part of the stent, and the temporary sutures 35 are removed.

After this fixation of leaflet assembly, the stent 40 of the valve is compressed from 25 mm diameter to 23 mm diameter and sterilized by using ethylenoxide sterilization.

Performance of valves made as described above was tested both in vitro and in vivo. Mechanical and functional testing of the prosthetic heart valve was performed in a simplified mock circulation. A BVS 5000 circulatory assist device (Abiomed, Danvers, Mass., USA) was included in a closed loop circuit having a reservoir and a return conduit. The heart pump bladder was driven by an Intra Aortic Balloon Pump (Maquet, Rastatt, Deutschland) with a frequency of 80 beats/min and output of 3600 cc/min, while afterload at the outflow side of the heart pump was set to 80 mmHg using a water column. In an initial test the standard valve of the heart pump at the outflow side was replaced by a valve constructed with three single leaflets made from woven fabric of 55 dtex UHMWPE yarn mounted in a transparent plastic conduit to study its open and closure behavior. This pilot valve sustained over 4 weeks (3.571.200 cycles) while remaining competent without deterioration of the woven leaflets. Build on this experience, a valve constructed as above (based on leaflets from woven fabric of 10 dtex UHMWPE yarn), was tested under equivalent physiologic loading conditions of the systemic human circulation, cumulatively during over 120 days (13.824.000 cycles). The valve opened fully into an optimal effective orifice, having commonly known vertical position of vibrating leaflets in parallel to the fluid stream, and closed while visually not revealing closure defects along the coaptation line of meeting free margins of leaflets, except from a tiny central hole of about 0.5 mm. Visual inspection after testing revealed a completely intact valve geometry; leaflets showing no fraying at the free margin or any other disruption or defects. All the suture lines as described above, as well as the knots were intact.

The prosthetic pulmonary valves were also implanted in adult sheep models (bread "swifter", body mass 55-70 kg) on the beating heart, while using an extra-corporeal circulation machine. Access to the pulmonary artery was achieved through left thoracotomy 3rd-4th i.c.s. The pulmonary artery was incised longitudinally, whereafter the native leaflets were cut out. Three positioning stitches of 5-0 Prolene® were used to pull on the commissural native posts. The valve was sutured into the pulmonary artery on the supra annular level (plane top of native commissures) using 5-0 Prolene®. The pulmonary artery was closed in linear fashion.

Echocardiography showed normal leaflet function without valvular or paravalvular regurgitation, apart from some occasional minimal regurgitation in the centre of the valve. The wound was closed and the sheep was taken to stables for recovery.

All treated sheep remained stable, without any adverse clinical signs up to 6 months observation periods. After this period the leaflet function was assessed again. Echocardiography showed adequate leaflet function with minor to moderate valvular but no paravalvular regurgitation, and there was no change in effective orifice since the day of implant. After this, the valves were taken out of the sheep for inspection. The leaflets and supporting elements were overgrown with tissue, but this appeared to be a very thin layer of fibroblasts and endothelial cells without histological and radiological signs of tissue calcification, and with a maximum thickness (including the leaflet) of 250 µm at the free edge with increasing amount of streamlining repair tissue towards the nadir. The mechanics of the valve appeared to be unaltered, all sutures were in place without fractures and the free margin of the leaflets appeared to be completely intact as originally made. No signs of fraying or other anomalies could be detected. The inventors are not aware of other studies using a prosthetic valve having leaflets made from a fabric woven from synthetic fibers, and wherein animals having such implanted valve survived a 6 months period without complications.

EXAMPLE 2

A prosthetic aortic valve to be implanted in the systemic circulation was made analogously to Example 1 with some modifications. The supporting element was prepared by taking out three half-moon pieces of fabric (facing the sinus valsalva in the human or animal aorta) to allow blood supply to flow into the coronary ostia. The remaining edge of the supporting element was fixed to the leaflet according to corresponding suture line of the U-shaped cusp suture line (facing the sinus valsalva). A second suture was used to complete attaching of the textile structure and create the actual leaflet assembly within the stent, by stitching to the stent posts 41 with a length of about 9 mm, and by stitching the leaflet layer to the supporting element layer and stent to create the valve cusps.

The valve was subsequently constructed in similar way as the pulmonary valve described here above. When completed, an additional sewing cuff of braided UHMWPE yarn was sutured with MaxBraid™ 3-0 UHMWPE (available from Teleflex, Limerick, Ireland), in an everted fashion using the Blalock stitch configuration.

Valves were implanted in adult sheep models (bread "swifter", body mass 65 kg) on the arrested heart under support of extra-corporeal circulation. Access to the aortic root was achieved through left thoracotomy 3rd-4th i.c.s. The pulmonary artery was dissected and pulled aside to allow transverse incision of the aorta. Classical implant was performed under cardiac arrest using a running suture Prolene® 5-0. The aorta was closed with a pericardial patch and the heart was defibrillated thereafter. The heart lung machine was disconnected. Echocardiography showed normal leaflet function without valvular or paravalvular regurgitation.

Any one of the embodiments, aspects and preferred features or ranges as disclosed in this application and relating to a method of making a prosthetic valve or a valve as obtainable by or as obtained with the method may be combined in any combination, unless stated otherwise herein or if technically clearly not feasible to a skilled person. The invention is further summarized in the below set of embodiments.

A method of making a prosthetic valve (400) that can take a first form wherein the valve is open and a second form wherein the valve is closed, the valve comprising a leaflet (3), a supporting element (2), and a stent (40) to which the leaflet and supporting element are attached, the leaflet having a free margin (5) that can move between a first position wherein the valve takes the first form and a second position wherein the valve takes the second form, the method comprising:
    providing a woven textile structure,
    forming the leaflet and the supporting element from the textile structure, such that a selvedge of the textile structure forms the free margin of the leaflet, and
    forming the valve therewith,
wherein the textile structure has a single layer thickness of between 40 to 150 µm and comprises yarn comprising polymeric filaments, the yarn having a linear density of less than 120 dtex and an elongation at break of 10% or less, and wherein the leaflet is attached to the stent by making stitches through at least 2 layers of the woven textile structure to form a commissure.

The method according to previous embodiment, wherein the textile structure has a layer thickness of at most 140, 130, 120, 110 or 100 µm and at least 50 or 60 µm, for example of between 50 to 100 µm.

The method according to any one of previous embodiments, the yarn has a linear density of less than 60, 50, 40, 30, 20 or even 15 dtex, preferably a linear density of at least 5, 7 or 10 dtex; for example a linear density of between 5 and 30 dtex, or between 7 and 15 dtex.

The method according to any one of previous embodiments, wherein the yarn has an elongation at break of less than 9, 8, 7, 6 or 5%, preferably between 1 and 5%.

The method according to any one of previous embodiments, wherein the yarn comprises ultra-high molecular weight polyethylene (UHMWPE) filaments, preferably at least 80 mass % UHMWPE filaments with a tenacity of at least 2 GPa.

The method according to previous embodiment, wherein the UHMWPE yarn is a gel-spun UHMWPE multifilament yarn having a Young's modulus of at least 30 GPa or 50 GPa, and preferably an elongation at break of about 2 to 4%.

The method according to any one of previous embodiments, wherein the yarn comprises at least 90 mass % UHMWPE filaments and preferably consists essentially of UHMWPE filaments.

The method according to any one of previous embodiments, wherein the prosthetic valve has one, two or three leaflets; preferably the valve has two or three leaflets, more preferably three leaflets.

The method according to any one of previous embodiments, wherein forming leaflet and supporting element comprises assembling and connecting multiple pieces of woven textile structure, forming multiple leaflets from one piece of woven textile structure and multiple supporting elements from another piece and then assembling and connecting, or forming multiple leaflets and supporting elements from a single woven textile structure.

The method according to any one of previous embodiments, wherein stitches are made through at least 3 layers of the woven textile structure, preferably through at least 4, 5, 6 or 7 layers and at most 12, 11 or 10 layers.

The method according to any one of previous embodiments, wherein the commissure runs substantially parallel to the longitudinal axis of the valve.

The method according to any one of previous embodiments, wherein the commissure extends over the full height of the stent, preferably the commissure has a length starting from the outflow side of about 5-12 mm, or of about 7-10 mm.

The method according to any one of previous embodiments, further comprising making a fold in at least one layer substantially parallel to the longitudinal axis of the valve before making stitches through layers of woven textile structure.

The method according to any one of previous embodiments, further comprising making a fold in at least one layer substantially orthogonal to the longitudinal axis of the valve before making stitches through layers of woven textile structure.

The method according to any one of previous embodiments, wherein the stitches are made using a yarn or suture material that has at least similar strength properties as the yarn comprised in the textile structure, preferably stitches are made using a yarn or a suture of suitable size or linear density and comprising at least 80 or 90 mass % or consisting essentially of UHMWPE yarn.

The method according to any one of previous embodiments, wherein the free margin of a leaflet has excess length relative to the minimum length needed for closing the valve of at least 5%, preferably of at least 7, 10 or 15%, and of at most 40 or 30%.

The method according to any one of previous embodiments, comprising providing one or more pieces of a flat woven textile structure having two selvedges and two edges without selvedge, and connecting the edges without selvedge to form a tubular structure.

The method according to any one of previous embodiments, comprising providing a single piece of a seamless tubular woven textile structure, and at least partly inverting the tubular structure. The method according to any one of previous embodiments, wherein the stent is a self-expandable stent.

A method for making a leaflet assembly for a prosthetic valve as described in any one of previous embodiments.

A prosthetic valve as obtainable by the method according to any one of previous embodiments.

A prosthetic valve (400) that can take a first form wherein the valve is open and a second form wherein the valve is closed, the valve comprising a leaflet (3), a supporting element (2), and a stent, wherein
    the leaflet has a free margin (5) that can move between a first position wherein the valve takes the first form and a second position wherein the valve takes the second form,
    the leaflet and the supporting element comprise a woven textile structure wherein a selvedge of the woven textile structure forms the free margin of the leaflet,
    the woven textile structure has a single layer thickness of between 40 to 150 μm and comprises yarn comprising polymeric filaments, the yarn having a linear density of less than 120 dtex and an elongation at break of 10% or less; and
    the leaflet is attached to the stent by stitches made through at least 2 layers of the woven textile structure.

The prosthetic valve according to previous embodiment, wherein the valve comprises two leaflets, the second leaflet acting as a closure surface for the first leaflet and vice versa, preferably the valve comprises three leaflets, each leaflet acting as a closure surface for the other two leaflets.

The prosthetic valve according to any one of previous embodiments, wherein the textile structure has a layer thickness of at most 140, 130, 120, 110 or 100 μm and at least 50 or 60 μm, for example of between 50 to 100 μm.

The prosthetic valve according to any one of previous embodiments, wherein the yarn has a linear density of less than 60, 50, 40, 30, 20 or even 15 dtex, preferably a linear density of at least 5, 7 or 10 dtex; for example a linear density of between 5 and 30 dtex, or between 7 and 15 dtex.

The prosthetic valve according to any one of previous embodiments, wherein the yarn has an elongation at break of less than 9, 8, 7, 6 or 5%, preferably between 1 and 5%.

The prosthetic valve according to any one of previous embodiments, wherein the yarn comprises ultra-high molecular weight polyethylene (UHMWPE) filaments, preferably at least 80 mass % UHMWPE filaments with a tenacity of at least 2 GPa.

The prosthetic valve according to previous embodiment, wherein the UHMWPE yarn is a gel-spun UHMWPE multifilament yarn having a Young's modulus of at least 30 GPa or 50 GPa, and preferably an elongation at break of about 2 to 4%.

The prosthetic valve according to any one of previous embodiments, wherein the yarn comprises at least 90 mass % UHMWPE filaments and preferably consists essentially of UHMWPE filaments.

The prosthetic valve according to any one of previous embodiments, wherein leaflet and supporting element are formed from multiple pieces of woven textile structure, or from a single woven textile structure.

The prosthetic valve according to any one of previous embodiments, wherein a leaflet is attached to the stent by stitches made through at least 3 layers of the woven textile structure, preferably through at least 4, 5, 6 or 7 layers and at most 12, 11 or 10 layers.

The prosthetic valve according to any one of previous embodiments, wherein the commissure runs substantially parallel to the longitudinal axis of the valve.

The prosthetic valve according to any one of previous embodiments, wherein the commissure extends over the full height of the stent, preferably the commissure has a length starting from outflow side of the valve of about 5-12 mm, or of about 7-10 mm.

The prosthetic valve according to any one of previous embodiments, further comprising a fold in a layer, the fold running substantially parallel to the longitudinal axis of the valve, through which the stitches are made.

The prosthetic valve according to any one of previous embodiments, further comprising a fold in a layer, the fold running substantially orthogonal to the longitudinal axis of the valve, through which the stitches are made.

The prosthetic valve according to any one of previous embodiments, wherein the stitches are made with a yarn or suture material that has at least similar strength properties as the yarn comprised in the textile structure, preferably the stitches are made with a yarn or a suture of suitable size or linear density and comprising at least 80 or 90 mass % or consisting essentially of UHMWPE yarn.

The prosthetic valve according to any one of previous embodiments, wherein the free margin of a leaflet has excess length relative to the minimum length needed for closing the valve, of at least 5%, preferably of at least 7, 10 or 15%, and of at most 40 or 30%.

The prosthetic valve according to any one of previous embodiments, comprising a tubular structure made from one or more pieces of a flat woven textile structure having two selvedges and two edges without selvedge, by connecting the edges without selvedge.

The prosthetic valve according to any one of previous embodiments, comprising a seamless tubular woven textile structure.

The prosthetic valve according to any one of previous embodiments, wherein the stent is a self-expandable stent.

A leaflet assembly for a prosthetic valve as described in any one of previous embodiments.

The invention claimed is:

1. A method of making a prosthetic valve that can take a first form wherein the valve is open and a second form wherein the valve is closed, the valve comprising a leaflet, a supporting element, and a stent to which the leaflet and supporting element are attached, the leaflet having a free margin that can move between a first position wherein the valve takes the first form and a second position wherein the valve takes the second form, the method comprising:
    (i) providing a woven textile structure having a single layer thickness of between 40 to 150 μm and comprising yarn comprising at least 80 mass % of ultra-high molecular weight polyethylene (UHMWPE) filaments having a tenacity of at least 2 GPa, the yarn having a linear density of at least 5 and less than 120 dtex, and an elongation at break of between 1and 5%,
    (ii) forming the leaflet and the supporting element from the textile structure such that a selvedge of the textile structure forms the free margin of the leaflet,
    (iii) forming the valve therewith, and
    (iv) attaching the leaflet to the stent by making stitches through at least three layers of the woven textile structure to form a commissure.

2. The method according to claim 1, wherein the textile structure has a layer thickness of between 50 to 100 μm.

3. The method according to claim 1, wherein the yarn has a linear density of less than 60 dtex.

4. The method according to claim 1, wherein the yarn is a gel-spun UHMWPE multifilament yarn having a Young's modulus of at least 30 GPa.

5. The method according to claim 1, wherein the yarn comprises at least 90 mass % UHMWPE filaments.

6. The method according to claim 1, wherein the prosthetic valve has one, two or three leaflets.

7. The method according to claim 1, wherein step (iv) is practiced by making stitches through at least four layers of the woven textile structure.

8. The method according to claim 1, wherein the commissure runs substantially parallel to a longitudinal axis of the valve and has a length starting from an outflow side of 5-12 mm.

9. The method according to claim 1, further comprising making a fold in at least one layer of the woven textile structure substantially parallel to a longitudinal axis of the valve before making the stitches through the layers of woven textile structure.

10. The method according to claim 1, further comprising making a fold in at least one layer of the woven textile structure substantially orthogonal to a longitudinal axis of the valve before making the stitches through the layers of woven textile structure.

11. The method according to claim 1, wherein the stitches are made using a yarn or suture material having a tenacity which is at least the same as the tenacity of the yarn of the woven textile structure.

12. The method according to claim 11, wherein the stitches are made using a suture which comprises at least 80 mass % of UHMWPE yarn.

13. The method according to claim 11, wherein the stitches are made using a suture which consists essentially of UHMWPE yarn.

14. The method according to claim 1, which comprises providing the free margin of the leaflet with an excess length relative to a minimum length needed for closing the valve of at least 5%.

* * * * *